United States Patent [19]

Hall et al.

[11] 4,186,103
[45] Jan. 29, 1980

[54] USE OF SPIROPYRAN DERIVATIVES IN AUGMENTING, ENHANCING OR MODIFYING THE AROMA OF DETERGENTS

[75] Inventors: John B. Hall, Rumson; Denis E. Hruza, Sr., Brick Town, both of N.J.; Edward J. Shuster, Brooklyn, N.Y.; Manfred H. Vock, Locust; Joaquin F. Vinals, Red Bank, both of N.J.

[73] Assignee: International Flavors & Fragrances Inc., New York, N.Y.

[21] Appl. No.: 27,949

[22] Filed: Apr. 6, 1979

Related U.S. Application Data

[60] Continuation-in-part of Ser. No. 765,629, Feb. 4, 1977, which is a division of Ser. No. 701,249, Jun. 30, 1976, abandoned, which is a continuation-in-part of Ser. No. 547,057, Feb. 4, 1975, abandoned.

[51] Int. Cl.² .............................................. C11D 3/50
[52] U.S. Cl. .......................... 252/174.11; 252/522 R; 252/108
[58] Field of Search .................. 252/522, 174.11, 108, 252/109

[56] References Cited

U.S. PATENT DOCUMENTS 4,076,853  2/1978  Light et al. ..................... 252/174.11

Primary Examiner—Mayer Weinblatt

Attorney, Agent, or Firm—Arthur L. Liberman; Franklin D. Wolffe

[57] ABSTRACT

Described are spiropyran derivatives for use in augmenting, enhancing or modifying the aroma of perfumed articles including detergents, said spiropyran derivatives having the structure:

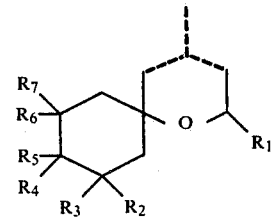

wherein $R_1$ is hydrogen or methyl; wherein $R_2$, $R_3$, $R_4$, $R_5$, $R_6$ and $R_7$ represents hydrogen or $C_1$–$C_5$ lower alkyl; wherein when one of $R_2$, $R_3$, $R_4$, $R_5$, $R_6$ or $R_7$ is any of $C_2$–$C_5$ lower alkyl, each of the other of the $R_2$, $R_3$, $R_4$, $R_5$, $R_6$ and $R_7$ moieties is hydrogen; wherein each of the dashed lines represents a carbon-carbon single bond or a carbon-carbon double bond, with at least one of the dashed lines being a carbon-carbon single bond. These detergents have green, floral, herbal, eucalyptol-like, sweet, minth and/or terpineol-like notes.

1 Claim, 7 Drawing Figures

EXAMPLE I

FRACTION 2 FROM EXAMPLE II

FIG.4
FRACTION 17 FROM EXAMPLE IV
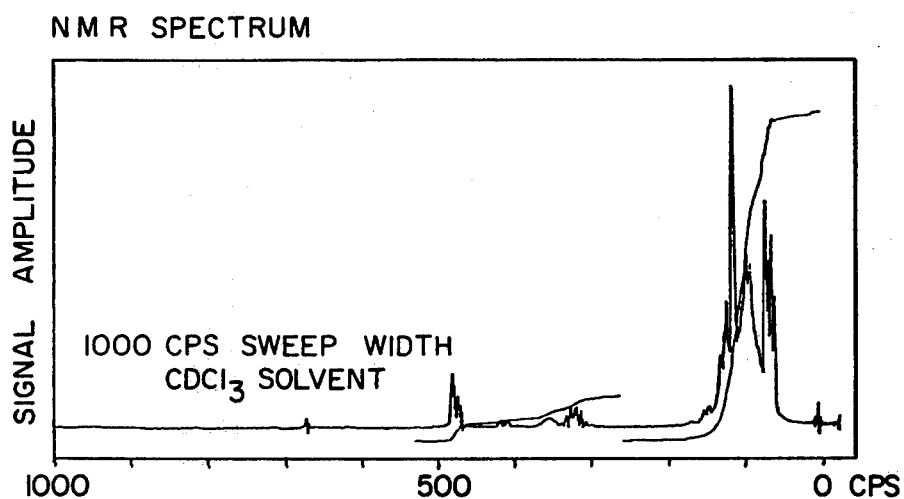
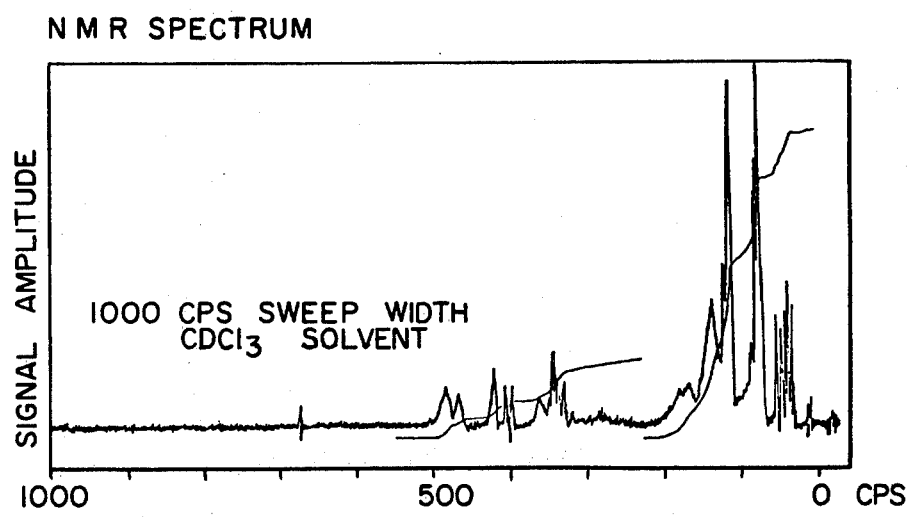
FIG.5
FRACTION 10 FROM EXAMPLE VII

FRACTION 13 FROM EXAMPLE IX

FRACTION 13 FROM EXAMPLE IX

USE OF SPIROPYRAN DERIVATIVES IN AUGMENTING, ENHANCING OR MODIFYING THE AROMA OF DETERGENTS

This application is a continuation-in-part of application for U.S. Pat. Ser. No. 765,629, filed on Feb. 4, 1977, which, in turn, is a divisional of application for U.S. Pat. Ser. No. 701,249, filed on June 30, 1976, now abandoned which in turn is a continuation-in-part of application for U.S. Pat. Ser. No. 547,057, filed on Feb. 4, 1975, now abandoned.

BACKGROUND OF THE INVENTION

The present invention relates to spiropyran derivatives having the structure:

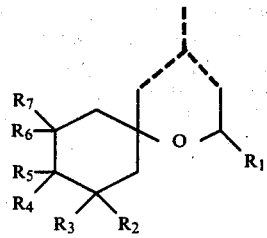

wherein $R_1$ is hydrogen or methyl; wherein $R_2$, $R_3$, $R_4$, $R_5$, $R_6$ and $R_7$ represents hydrogen or $C_1$-$C_5$ lower alkyl; wherein when one of $R_2$, $R_3$, $R_4$, $R_5$, $R_6$ or $R_7$ is any of $C_2$-$C_5$ lower alkyl, each of the other of the $R_2$, $R_3$, $R_4$, $R_5$, $R_6$ and $R_7$ moieties is hydrogen; wherein each of the dashed lines represents a carbon-carbon single bond or a carbon-carbon double bond, with at least one of the dashed lines being a carbon-carbon single bond, to augment, enhance or modify the aroma of detergents including anionic, cationic and non-ionic solid and liquid detergents. Included in the term "detergents" are soaps.

There has been considerable work performed relating to substances which can be used to impart (or enhance) flavors to (or in) various consumable materials. These substances are used to diminish natural materials, some of which may be in short supply, and to provide more uniform properties in the finished product. Dill, basil, valerian oil-like, caraway seed-like, thyme-like, piney, raspberry-like, blackberry-like, camphoraceous, herbaceous, eucalyptol-like, cooling, minty, ionone, tea-like, floral, sweet, fruity, woody, apple-like, petitgrain-like, smokey, leafy and green flavor notes or combinations of these for improving the taste and aroma of artificial raspberry or other berry fruit flavoring compositions or tea flavor or synthetic "menthe oil" compositions are particularly desirable for many uses in consumable articles, e.g., foodstuffs. Green, floral, herbal, eucalyptol-like, sweet, minth and terpineol-like notes are particularly desirable in perfume compositions. Aromatic, sweet, minty and cooling notes are particularly desirable in tobacco.

Chemical compounds having the pyran ring are known to be useful in flavor and fragrance compositions. Thus, published Japanese application 7 4011-073 (March 14, 1974) Mitshi Toatsu Chemicals Inc. discloses 2,5-diethyltetrhydropyran perfumes having rose-like perfume, and good stability in air, sunlight and humidity. Maltol, having the generic name: 3-hydroxy-2-methyl(1,4-pyran) is disclosed in "Perfume and Flavor Chemicals", Arctander Vol. II, #1831, to have "a warm-fruity, caramellic-sweet odor with emphasis on the caraway note in the dry state". Saturated polycyclic ethers are disclosed in Chodroff, et al. U.S. Pat. No. 3,417,107 to have attractive ambergris notes as well as a high degree of persistence. The structures of such polycyclic ethers are as follows:

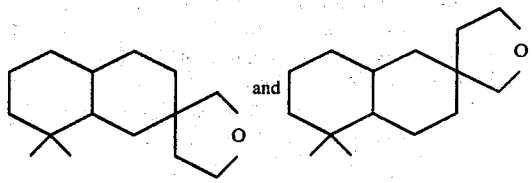

The structures of the compounds in a mix of unsaturated compounds which are precursors of the Chodroff, et al. perfumery compounds are as follows:

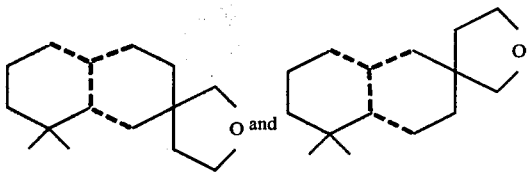

wherein one of the dashed lines represents a carbon-carbon double bond and the other of the dashed lines represents a single carbon.

U.S. Pat. No. 2,422,648 sets forth methods for producing a number of the compounds found to be useful in our invention thus, for example, examples III and IV at columns 6 and 7 of 2,422,648 are as follows:

EXAMPLE III

A mixture of about 150 parts by weight of 4-methyl-4-pentene-2-ol and about 147.2 parts by weight of cyclohexanone with about 200 parts by weight of benzene and about 2 parts by weight of p-toluenesulfonic acid was refluxed under a column for approximately four and one-half hours at about 94° C. to about 100° C. removing water by azeotropic distillation. Distillation of the neutralized reaction mixture gave about 191. 8 parts by weight of material of boiling point 80° C. to 90° C. at 10 mm., from which was obtained the composition corresponding to the formula $C_{12}H_{22}O$ boiling at 87.4° C. at 10 mm. which consists substantially of 2,4-dimethyl-6,6-pentamethylene-5,6-dihydro-1,2-pyran.

EXAMPLE IV

A mixture consisting of about 210 parts by weight of 3,3,5-trimethylcyclohexanone, about 150 parts by weight of 4-methyl-4-pentene-2-ol, about 250 parts by weight of benzene, and about 2 parts by weight of p-toluenesulfonic acid was refluxed under a column at about 91° C. to 97° C. for approximately 10 hours with removal of water by azeotropic distillation. Neutralization and distillation of the reaction mixture gave about 182.3 parts by weight of material having a boiling point of 90° C. to 96° C. at 5 mm, from which was obtained the product having the elemental composition indicated by the formula $C_{15}H_{26}O$ boiling at 94.6° C. at 5 mm. and consisting substantially at 2,4-dimethyl-6,6-(2',2',4'-trimethylpentamethylene)-5,6-dihydro-1,2-pyran.

In addition U.S. Pat. No. 2,422,648 at column 5 lines 34-55 states:

"The unsaturated cyclic ethers prepared by the process of the invention are useful as diluents, modifying agents, and processing reagents in the textile industry, and the higher members particularly are valuable as solvents. They may also be used as reagents and/or additives in the formation of synthetic resins, plastics and synthetic rubbers and the higher members may serve as insecticides, fungicides, parasiticides or as constituents of insecticidal, fungicidal and parasiticidal compositions, etc. In addition, they are valuable intermediates in the syntheses of valuable organic products; for example, the substituted dihydropyrans may be hydrogenated, if desired in the presence of a suitable hydrogenation catalyst such as Raney nickel, to produce a novel substituted tetrahydropyran compounds having the formula:

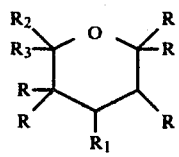

(wherein the R's represent hydrogen or non-olefinic hydrocarbon".

No disclosure of the olfactory properties of such pyran compounds is set forth in U.S. Pat. No. 2,422,648.

Dutch published application No. 6,808,496 published on Dec. 19, 1969 (corresponding to British Pat. No. 1,281,813 published on July 19, 1972) discloses, for use in perfumery in order to provide fruity green scents with an overtone of floral muguet, compounds having the structure:

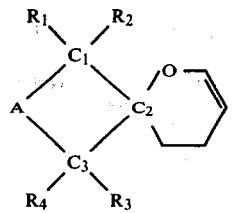

wherein A together with the carbon atoms $C_1$, $C_2$ and $C_3$, forms a cyclic system which may either be monocyclic or polycyclic, e.g. bicyclic or tricyclic, and may carry one or more alkyl groups on the residue A; and $R_1$ to $R_4$ represent hydrogen atoms or alkyl groups having 1 to 5 carbon atoms with the exception that at least one of $R_1$ to $R_4$ represents an alkyl group when A represents a 1,2-ethylidene or 1,3-propylidene group. More specifically, structures 15, 16, 17, 18, 19, 20, 25 and 26 of the published Dutch application No. 6,808,496 are as follows:

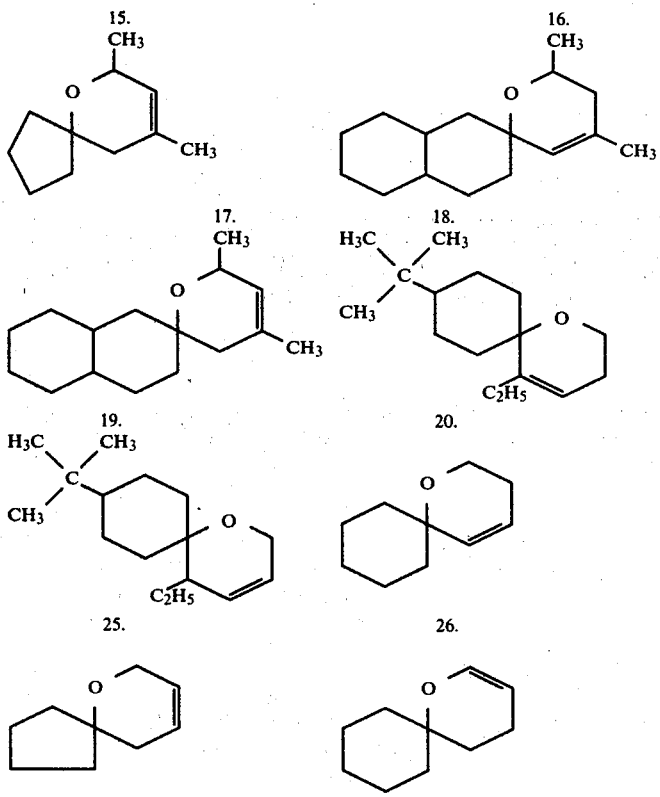

The chemicals defined by these structures are different in kind from the chemical compounds of the instant invention and their fragrance properties are different in kind from those of the instant invention, which are considered to have unexpected, advantageous properties from the standpoint of quality or character of fragrance when used with other perfumery materials and in connectin with perfumed articles and colognes.

William, et al, J. Am. Chem. Soc., 72, 5738—43 (1950) sets forth the following reaction sequence:

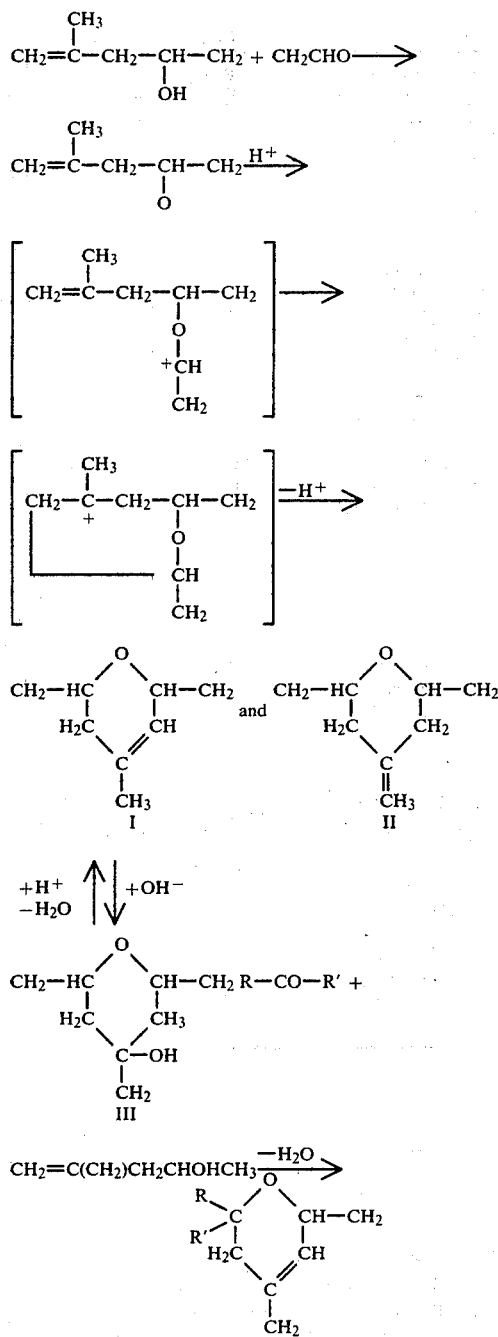

Nowhere in the Williams, et al. article is there a disclosure of the compounds covered by the claims herein which define the instant invention. Indeed, tertiary alcohols which might be with 4-methyl-4-penten-2-ol or by reacting 3,3,5-trimethyl-cyclohexanone with 4-methyl-4-penten-2-ol are not believed to have been formed "in situ." The Williams, et al, article shows that the cycloalkanone and 4-methyl-4-penten-2-ol are reacted in the presence of a benzene solvent where the benzene is indicated on age 5742, right-hand column, to have been added to the reaction mixture:

" ... in order to maintain a reaction temperature in the neighborhood of 90°-100° C. and to remove water azeotropically as formed ... "

It is noteworthy that when using such an azeotroping agent as benzene or cyclohexane, little if any tertiary hydroxyl compound is formed; particularly in the case of the t-butyl derivative claimed herein.

THE INVENTION

It has now been discovered that novel solid and liquid anionic, cationic or non-ionic detergents including soaps having green, floral, herbal, eucalyptol-like, sweet, minty and terpineol-like notes can be created by the utilization of spiropyran material having the structure:

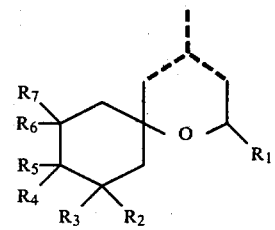

wherein $R_1$ is hydrogen or methyl; wherein $R_2$, $R_3$, $R_4$, $R_5$, $R_6$ and $R_7$ represents hydrogen or $C_1$-$C_5$ lower alkyl; wherein when one of $R_2$, $R_3$, $R_4$, $R_5$, $R_6$ or $R_7$ is any of $C_2$-$C_5$ lower alkyl, each of the other of the $R_2$, $R_3$, $R_4$, $R_5$, $R_6$ and $R_7$ moieties is hydrogen; wherein each of the dashed lines represents a carbon-carbon single bond or a carbon-carbon double bond, with at least one of the dashed lines being a carbon-carbon single bond in detergent compositions including solid and liquid anionic, cationic or non-ionic detergent powders. The term "detergent" includes "soaps".

A number of the spiropyrans so useful are novel, themselves and such novel compounds are defined by the following generic structure:

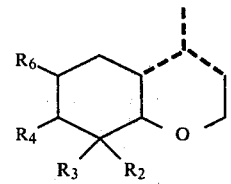

wherein $R_2$, $R_3$ and $R_6$ are each selected from the group consisting of hydrogen and methyl; wherein $R_4$ is selected from the group consisting of t-butyl and hydrogen; wherein when $R_4$ is t-butyl, $R_2$, $R_3$ and $R_6$ are each hydrogen; wherein each of the dashed lines represents a carbon-carbon single bond or a carbon-carbon double bond, with at least one of the dashed lines being a carbon-carbon single bond.

The following table sets forth examples of a number of the spiropyrans useful in the practice of our invention, as well as their olfactory properties:

TABLE I

| Spiropyran Material | Structure Representation | Flavor Properties | Fragrance Properties |
|---|---|---|---|
| (i) Mixture of 4-methylene-1-oxaspiro(5,5)undecane, 4-methyl-1-oxaspiro(5,5)undec-1-ene and 4-methyl-1-oxaspiro(5,5)undec-4-ene | | A dill, basil, valerian oil aroma with caraway nuances and dill, basil, valerian oil taste with a thyme-like and piney character. | Ready, green, basil, floral, herbal and eucalyptol notes. |
| (ii) Mixture of 2,4-dimethyl-1-oxaspiro(5,5)undec-1-ene, 2,4-dimethyl-1-oxaspiro(5,5)undec-4-ene and 2-methyl-4-methylene-1-oxaspiro(5,5)undecane | | Ionona, tea, and red-berry aroma with herbaceous, "damascenone-like," floral, sweet, fruity, woody and apple-like nuances and woody, petitgrain-like, fruity taste with apple-like, smokey and astringent notes. | Green, herbaceous, sweet, oily, slightly minty aroma with "pickled," green olive top notes. |
| (iii) Mixture of 9,8,10-trimethyl-4-methylene-1-oxaspiro(5,5)undecane, 4,8,8,10-tetramethyl-1-oxaspiro(5,5)undec-1-ene and 4,8,8,10-tetramethyl-1-oxaspiro(5,5)undec-4-ene | | Green, leafy, minty, parsley-like aroma with green, minty, herbaceous parsley-like flavor. | Green, floral, minty and tarpinol-like notes. |
| (iv) Mixture of 5-t-butyl-4-methylene-1-oxaspiro(5,5)undecane, 4-methyl-5-t-butyl-oxaspiro(5,5)undec-1-ene and 4-methyl-4-r-butyl-1-oxaspiro(5,5)undec-4-ene | | Salicylate floral aroma with a green/woody undertone and a salicylate-like, oily floral herbaceous taste. | Green, floral and warm limal notes. |
| (v) 4-methyl-1-oxaspiro(5,5)undecane | | Sweet, floral, fruity, minty, vanillin-like aroma with blackberry, berry and herbaceous notes, and a minty, cooling taste with eucalyptol, piney, basil and herbaceous notes. | Basil, herbaceous, and eucalyptol notes. |

Specifically preferred compounds to be prepared according to the process of our invention and using the intermediates of our (i) 4-methyl-1-oxaspiro[5.5]undecane; and
(ii) the mixture of 9-t-butyl-4-methylene-1-oxaspiro[5.5]undecane, 4-methyl-9-t-butyl-1-oxaspiro[5.5]undec-3-ene and 4-methyl-9-t-butyl-1-oxaspiro[5.5]undec-4-ene.

The dashed lines in each of the structures of the structure representations of Table I represent double bonds. Where two dashed lines are set forth in the same structure, a mixture of double bond isomers is indicated.

For the purposes of our invention, where possible the foregoing structures are intended to cover the "dextro", "laevo" and mixtures of "dextro" and "laevo" stereoisomers (where saturated spiropyran derivatives are involved) as well as the "cis", "trans" and mixtures of "cis" and "trans" isomers of the spiropyrans useful in practicing our invention.

A novel process for the preparation of spiropyrans useful in practicing our invention, having the structure:

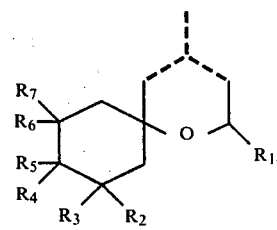

involves initially producing a mixture of unsaturated and hydroxy-substituted spiropyrans according to the following reaction:

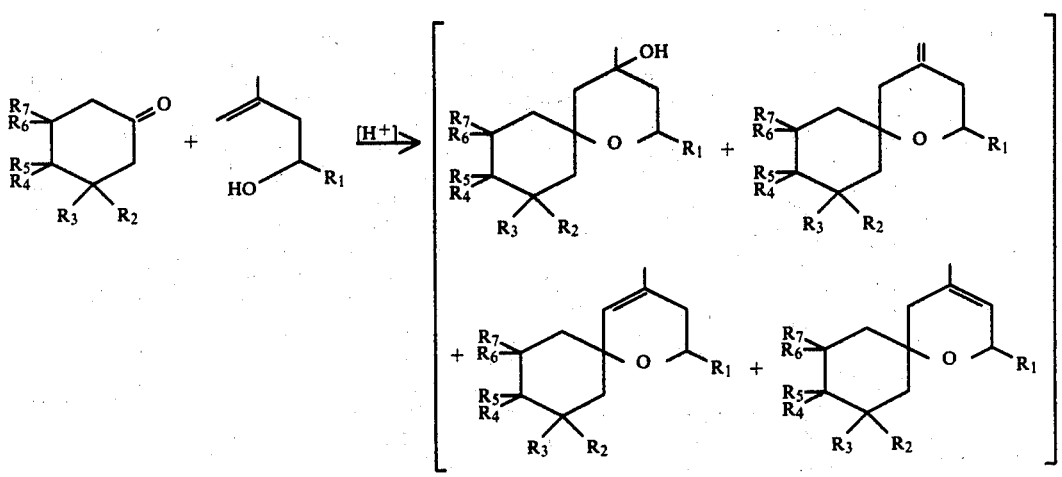

then separating (by means of fractional distillation) the hydroxy-substituted spiropyrans from the unsaturated spiropyrans; and finally dehydrating the hydroxy-substituted spiropyrans in the presence of a dehydrating agent to form additional amounts of unsaturated spiropyrans.

This process differs from the process of the prior art as set forth in U.S. Pat. No. 2,422,648 (Williams, et al) in that the Williams, et al. process involves removal of water of reaction by azeotropic distillation thereby creating a situation whereby little, if any, hydroxyl derivative is produced. The drawback of the Williams, et al. process is the involvement of an entraining agent such as benzene in the reaction mass, which would leave traces of benzene in the reaction mass thereby rendering the final reaction product unsuitable for use in the foodstuff flavor, fragrance or tobacco flavor fields. On the other hand, the process of our invention fulfills the need for obtention of high yields of spiropyran taken together with the need for producing a non-toxic spiropyran derivative.

The overall reaction sequence illustrating the process of our invention is as follows:

STEP I

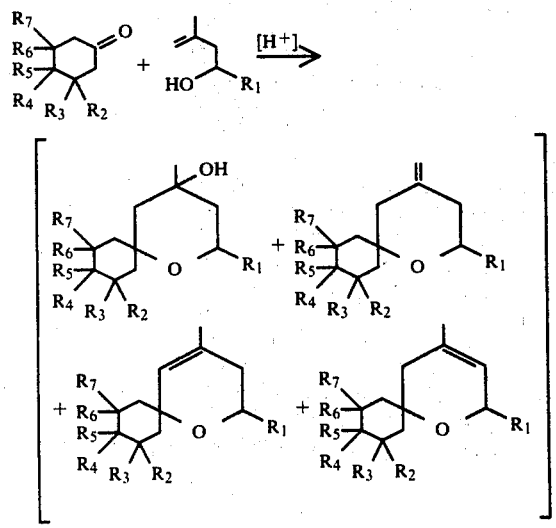

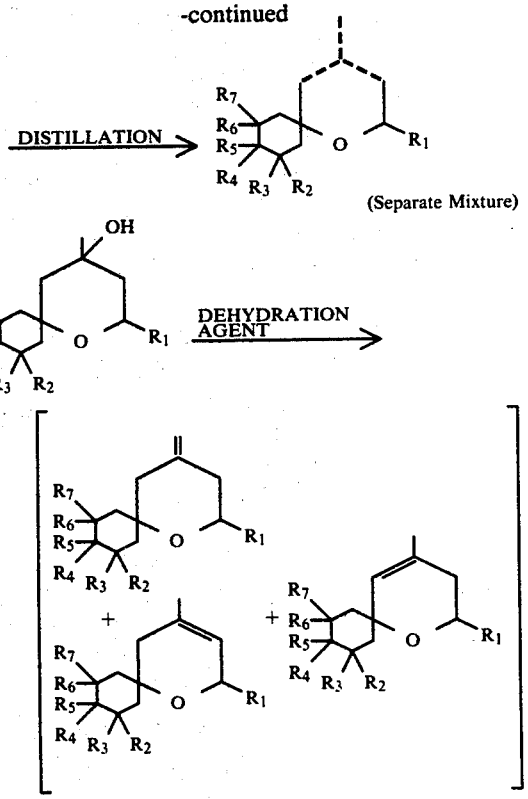

The hydroxy-substituted spiropyrans used as reaction intermediates are novel compounds.

The dehydration product is then admixed with the unsaturated spiropyran distillation product thereby giving rise, overall, to a high yield of product.

The initial reaction may be carried out at temperatures from 20° C. up to 140° C. and it preferably takes place at temperatures in the range of 80°–110° C. and autogeneous pressure. Thus, for example, where cyclohexanone is reacted with 3-methyl-3-buten-1-ol, the reaction is carried out at a temperature in the range of from 80°–85° C. at one atmosphere pressure.

In the initial reaction, solvents such as cyclohexane, benzene or toluene are to be avoided in order to avoid resultant residual traces of solvent in the desired product.

The initial reaction is carried out in the presence of a protonic acid catalyst, for example, concentrated (92%) sulfuric acid; para-toluenesulfonic acid; or benzene sulfonic acid.

It is preferred that the substituted alkenol reactant be initially admixed at low temperatures (e.g., 10° C.) with the acid catalyst. It is also preferable that the cyclohexanone reactant be preheated to the desired reaction temperature prior to reaction. The substituted alkenol-acid catalyst mixture is then added dropwise with stirring to the cyclohexanone or substituted cyclohexanone reactant.

The mole ratio of cyclohexanone reactant to substituted alkenol reactant is preferably approximately 1:1, an excess of either reactant requiring additional separation time at the end of the reaction. The time of reaction varies from 30 minutes to 10 hours depending upon the temperature of reaction. Higher temperatures of reaction (short of decomposition or pyrolysis temperatures) give rise to shorter required times for the completion of the reaction.

After the separation of the unsaturated spiropyran from the hydroxy-substituted spiropyran by means of fractional distillation, the hydroxy-substituted spiropyran is dehydrated by placing said hydroxy-substituted spiropyran in a reaction vessel containing dehydration agent, e.g., $KHSO_4$ or p-toluenesulfonic acid and distilling the reaction product, the unsaturated spiropyran, through a distillation column. As the unsaturated spiropyran distills, the dehydration reaction in the reaction vessel proceeds. The temperature of distillation and reaction temperature are functions of ambient pressure and nature of the particular hydroxy-substituted spiropyran being dehydrated. Preferably the dehydration is carried out at low vacuum. A pressure of the order of 15 mm Hg is preferred.

The weight percent of dehydration agent based on hydroxy-substituted spiropyran, may vary from about 2% up to about 10% by way of the hydroxy-substituted spiorpyran with the percentage of about 5% dehydration catalyst being preferred.

FIG. 1, is a schematic block diagram setting forth the steps of the novel process of our invention.

If desired, the unsaturated spiropyran resulting from the foregoing process steps may be hydrogenated in the presence of a palladium on carbon catalyst at a temperature in the range of 20° C.–150° C. and a pressure in the range of 50–2000 psig in an inert solvent such as isopropyl alcohol. The lower range of hydrogenation temperatures and pressures give satisfactory yields when only one methyl substituent is located on the pyran ring. A larger number of substituents on the pyran ring requires more stringent hydrogenation conditions.

When the spiropyran derivatives of our invention are used as food flavor adjuvants, the nature of the coingredients included with the said spiropyran derivatives in formulating the product composition will also serve to alter the organoleptic characteristics of the ultimate foodstuffs treated therewith. As used herein in regard to flavor, the term "alter" in its various forms means "supplying or imparting flavor character or note to otherwise bland, relatively tasteless substance or augmenting or enhancing the existing flavor characteristics where a natural flavor is deficient in some regard or supplementing the existing flavor impression to modify its quality, character or taste". As used herein, the term "foodstuff" includes both solid and liquid ingestible materials which usually do, but need not have nutritional value. Thus, foodstuffs include meats, gravies, soups, convenience foods, beverages, dairy products, candies, vegetables, cereals, soft drinks, snacks, chewing gum, chewable vitamin tablets and the like.

Substances suitable for use herein as coingredients or flavoring adjuvants are well known in the art for such use being extensively described in the relevant literature. Apart from the requirement that any such material be "ingestibly" acceptable and thus non-toxid or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan; cellulose; and cellulose derivatives such as carboxymethyl cellulose and methyl cellulose; natural and synthetic gums such as gum arabic, gum tragacanth; gelatin, proteinaceous materials, lipids; carbohydrates; starches pectins, and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monosterate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources, such as zinc chloride, zinc sulfate and the like.

Other flavorants and flavor intensifiers include organic acid, e.g., fatty saturated acids, unsaturated acids and amino acids; alcohols, e.g., primary and secondary alcohols, esters; carbonyl compounds, e.g., aldehydes and ketones as well as lactones; cyclic organic materials including benzene derivatives, isocyclics, heterocyclics such as furans particularly 2,5-dimethyl-3-acetyl furan and 2-methyl-2,3-dihydro furan-3-one, pyridines, pyrazines (particularly monoalkyl, dialkyl, trialkyl and tetraalkyl substituted pyrazines) and the like, sulfur-containing materials including thiazoles, disulfides, thiols, sulfides, aldehydes (for example, 3-phenyl-4-pentenal, 3-phenyl-3-pentenal, 3-phenyl-2-pentenal, 2-phenyl-2-pentenal and 2-phenyl-3-methyl-2-butenal); tri-sulfides and the like; other flavor potentiators such as monosodium glutamate, guanylates, inosinates, natural and synthetic flavorants such as vanillin, ethyl vanillin, diacetyl, phenethyl-2-furoate, maltol, natural gums and the like; spices, herbs, essential oils and extractives including "bitterness principles" such as theobromine, caffeine, naringin and other suitable materials creating a bitter effect.

The specific flavoring adjuvant selected for use may be either solid or liquid depending upon the desired physical form of the ultimate product, i.e., foodstuff, whether simulated or natural, and should, in any event, be capable of providing an environment in which the spiropyran material can be dispersed or admixed to provide a homogeneous medium. In addition, selection of one or more flavoring adjuvants as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of spiropyran material employed in a particular instance can vary over a relatively wide range whereby to its desired organoleptic effects. All parts and percentages given herein are by weight unless otherwise specified. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of spiropyran material will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions it has been found that quantities of spiropyran material ranging from a small but effective amount, e.g., 0.5 parts per million up to about 0.1% (1000 parts per million) by weight based on total composition are suitable. Concentrations in excess of the maximum quantity stated are not normally recommended since they fail to provide commensurate enhancement of organoleptic properties. In those cases, wherein the spiropyran material is added to the foodstuff as an integral component of the flavoring composition, it is, of course, essential that the total quantity of flavoring composition employed be sufficient to yield an effective spiropyran material concentration in the foodstuff product.

Food flavoring compositions prepared in accordance with the present invention preferably contain the spiropyran material in concentrations ranging from about 0.001% up to about 10% by weight based on a total weight of said flavoring composition.

The compositions described herein can be prepared according to conventional techniques well known as typified by cake batters and fruit juices and vegetable juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the spiropyran material with for example gum arabic, gum tragacanth, carrageenan and the like and thereafter spray-drying the resultant mixture whereby to obtain the particular solid product. Pre-prepared flavor mixes in powder form, e.g., a red currant mix or a berry fruit (e.g., red raspberry) flavored powder obtained by mixing dried solid components, e.g., starch, sugar, and the like and one or more of the spiropyran materials of our invention in a dry blender until the requisite degree of uniformity is achieved.

It is presently preferred to combine one or more of spiropyran materials of our invention with the following adjuvants:

Organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl, beta, beta-dimethylacrolein, hexanal, 2-hexenal, cis-3-hexenal, 4(p-hydroxyphenyl)-2-butanone, alpha-ionone, beta-ionone, and 2-pentenal; alcohols, such as 1-butanol, trans-2-buten-1-ol, ethanol, geraniol, 1-hexanol, cis-3-hexen-1-ol, 3-methyl-3-buten-1-ol, 1-pentanol, 1-penten-3-ol and 2-(4-hydroxy-4-methyl pentyl) norbornadiene; esters, such as butyl acetate, ethyl acetate, ethyl butyrate, ethyl crotonate, ethyl propionate, 2-hexenyl acetate, 2-hexenyl butyrate, hexyl acetate, hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate and terpenyl acetate, essential oils such as jasmine absolute, rose absolute, orris absolute, lemon essential oil and vanilla; lactones; sulfides, e.g., methyl sulfide and other materials such as maltol and citral, as well as natural raspberry oil.

One or more the spiropyran materials of our invention and an auxiliary perfume ingredient, for example, alcohols, aldehydes, nitriles, esters, cyclic esters, and natural essential oils may be admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odourous substances which lend a particular note to the perfume throughout all stages of evaporation and substances which retard evaporation; and (d) topnotes which are usually low boiling fresh smelling materials.

In perfume compositions, the individual component will contribute its particular olfactory characteristics but the over-all effect of the perfume composition will be the sum of the effects of each of the ingredients. Thus, one or more of the spiropyran materials of our invention can be used to alter the aroma characteristics of a perfume composition, for example, by utilizing or moderating the olfactory reaction contributed by another ingredient in the composition.

The amount of the spiropyran material of our invention which will be effective in perfume compositions depend on many factors including the other ingredients, their amounts and the effects which are desired. It has been found that perfume compositions containing as little as 0.05% of one or more of the spiropyran materials of our invention or even less can be used to impart a green, floral, and herbaceous aroma found in hyacinth; or a green, minty aroma essential to geranium bourbon or a green, herbal aroma essential to basil, to soaps, cosmetics, and other products. The amount employed can range from 1% up to 100% of the fragrance components and will depend on considerations of cost, nature of the end product, the effect desired in the finished product and the particular fragrance sought.

The spiropyran materials of our invention are useful in perfume compositions as olfactory components in detergents, and soaps; space odorants and deodorants; perfumes; colognes; toilet water; bath preparations such as bath oils and bath solids; hair preparations such as lacquers, brilliantines, pomades and shampoo; cosmetic preparations such as creams, deodorants, hand lotions and sunscreens; powders such as talcs, dusting powders, face powders and the like. When used as an olfactory component of a perfumed article, as little as 100 parts per million of one or more of the spiropyran materials of our invention will suffice to impart green, basil, floral, herbal, eucalyptol-like, sweet oily and minty aromas thereto. Generally, no more than 3.0% of one or more of the spiropyran materials of our invention based on the ultimate end product is required in the perfume composition.

Futhermore, no more than 3.0% of one or more of the spiropyran materials of our invention based on the ultimate detergent composition of our invention is required in said detergent composition. Thus, the amount of spiropyran material contained in the detergent composition, whether contained in a perfume composition which in turn is intimately admixed with a detergent powder or whether contained by itself in said detergent composition may range from about 100 parts per million of said spiropyran materials up to about 3.0% by weight of the detergent powder. Such detergent powders may be anionic, cationic or non-ionic detergents which may be either solid or liquid.

In addition, the spiropyran derivatives of our invention may also be used in conjunction with other perfumery materials or may be used alone in deodorant compositions or in compositions intended to be used as deodorants wheren the spiropyran derivative is not only the effective perfuming ingredient but also is the effective deodorizing ingredient as well. In cases where the spiropyran derivative is to be used as the effective deodorizing ingredient and perfume ingredient in deodorizing compositions, e.g. deodorant sticks, the amount of spiropyran derivative may vary from 0.01% up to about 3% by weight of the overall deodorizing composition or composition intended to be used as a "deodorant".

In addition, the perfume composition or fragrance composition of this invention contain a vehicle or carrier for the spiropyran material. The vehicle can be a liquid such as an alcohol, a non-toxic alcohol, a non-toxic glycol or the like. The carrier can also be an absorbent solid such as a gum (e.g., gum arabic) or components for encapsulating the composition (such as gelatine).

It will thus be apparent that one or more of the spiropyran materials of our invention can be utilized to alter the sensory properties, particularly organoleptic properties such as flavor and/or frgrances of a wide variety of consumable materials.

An additional aspect of our invention provides an organoleptically improved smoking tobacco product and additives therefor as well as methods of making the same which overcome specific problems heretofore encountered in which specific desired aromatic, sweet, minty and "cooling" flavor characteristics are created or enhanced and may be readily controlled and maintained at the desired uniform level regardless of variations in the tobacco components of the blend; or the nature of the filter used in conjunction with the tobacco article.

This invention further provides improved tobacco additives and additives for materials used in the fabrication of tobacco articles and methods whereby desirable sweet, aromatic, minty and "cooling" flavor characteristics may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the spiropyran materials of our invention.

In addition to the spiropyran materials of our invention, other flavoring and aroma additives may be added to the smoking tobacco material or substitute therefor either separately or in mixture with one or more of the spiropyran materials;

I. Synthetic Materials

Beta-methyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1,2-methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a-6,6,9a-tetramethyl naphtho-(2,1-b)-furan;
4-Hydroxy hexanoic acid, gamma lactone;
Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil;

Origanum oil

An aroma and flavoring concentrate containing one or more of the spiropyran materials of our invention and, if desired, one or more of the above indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of sweet, minty, aromatic and "cooling" notes, we have found that satisfactory results are obtained if the proportion by weight of the sum total of spiropyran material to smoking tobacco material is between 50 ppm and 500 ppm (0.005%–0.05%) of the active ingredients to the smoking tobacco material. We have further found that satisfactory results are obtained if the proportion by weight of the sum total of spiropyran material used to flavoring material is between 0.05 and 0.50.

Any convenient method for incorporating the spiropyran material in the tobacco product may be employed. Thus, the spiropyran material taken alone or along with other flavoring additives may be dissolved in a suitable solvent such as ethanol, pentane, diethyl ether and/or other volatile organic solvents and the resulting solution may either be spread on the cured, cased and blended tobacco material or the tobacco material or filter may be dipped into such solution. Under certain circumstances, a solution of spiropyran material taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more spiropyran materials of our invention in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of 2,4-dimethyl-1-oxaspiro(5.5)undec-3-ene in an amount to provide a tobacco composition containing 800 ppm by weight of 2,4-dimethyl-1-oxaspiro (5.5)undec-3-ene on a dry basis. Thereafter, the alcohol is removed by evaporation and the tobacco is manufactured into cigarettes by the usual techniques. The cigarette when treated as indicated has a desired and pleasing aromatic, minty and "cooling" aroma which is detectable in the main and side streams when the cigarette is smoked.

While our invention is particularly useful in the manufacture of smoking tobacco, such as cigarette tobacco, cigar tobacco, and pipe tobacco, other tobacco products formed from sheeted tobacco dust or fines may also be used. As stated supra, the spiropyran materials of our invention can be incorporated with materials such as filter tip materials, seam paste, packaging materials and the like which are used along with the tobacco to form a product adapted for smoking. Furthermore, the spiropyran materials of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

The following examples are given to illustrate embodiments of the invention as it is presently preferred to practice it. It will be understood that these examples are illustrative, and the invention is not to be considered as restricted thereto except as indicated in the appended claims. All parts and percentages are by weight unless otherwise indicated.

EXAMPLE I

PREPARATION OF MIXTURE OF 4-METHYLENE-1-OXASPIRO(5.5)UNDECANE, 4-METHYL-1-OXASPIRO(5.5)UNDEC-3-ENE, 4-METHYL-1-OXASPIRO(5.5)UNDEC-4-ENE AND 4-HYDROXY-4-METHYL-1-OXASPIRO(5.5)UNDECANE

Reaction:

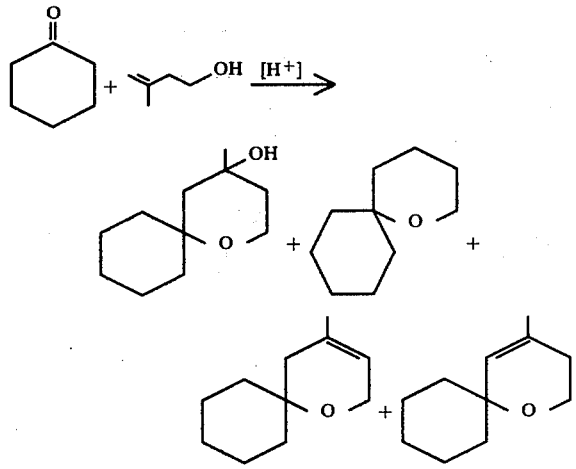

Into a 500 ml reaction flask equipped with stirrer, thermometer, reflux condenser and addition funnel is placed 98 gms. (1 mole) of cyclohexanone which is then heated to 80° C. and maintained at that temperature. In a separate reaction vessel is placed 86 gms. (1 mole) of 3-methyl-3-buten-1-ol and 1 gm. of concentrated sulfuric acid is added thereto dropwise while maintaining the temperature of 10° C. The resulting mixture of sulfuric acid and 3-methyl-3-buten-1-ol is then added over a period of 45 minutes to the cyclohexanone while maintaining the reaction mass temperature in the range of 80°–85° C.

After the addition, the reaction mass is stirred maintaining its temperature at 80°–85° C. for a period of 6 hours.

The reaction mass is then cooled to room temperature and is washed with a 100 ml portion of 10% aqueous sodium hydroxide. The aqueous phase is then extracted with one 50 ml portion of cyclohexane. The reaction mass is then combined with the cyclohexane extract and the resultant material is washed with one 100 ml portion of 10% sodium chloride solution.

The crude reaction product is stripped and rushed over after adding thereto 10 gms. of Primol ® (See Note 1) and 0.1 gms. of Ionol ® (See Note 2) at a vapor temperature of 57°–136° C., a liquid temperature of 105°–200° C. and a vacuum of 15.0–0.75 mm Hg.

Note 1: Primol ® is a registered trademark identifying a hydrocarbon mineral oil produced by Exxon Incorporation of Linden, New Jersey.
Note 2: Ionol ® is a registered trademark identifying the compound 2,6-di-t-butyl-4-methyl phenol.

The rushed over material is then fractionated after adding thereto 4.5 gms. of Primol ®, 0.1 gms. of Ionol ® and 0.5 gms. of triethanolamine as follows:

| Fraction No. | Vapor Temp. | Liquid Temp. | Pressure (mm Hg) | Weight of Fraction | Reflux Ratio |
|---|---|---|---|---|---|
| 1 | 49–55° C. | 119–123° C. | 15 | 4.7 | 20:1 |
| 2 | 105 | 125 | 15 | 6.9 | 20:1 |
| 3 | 105 | 128 | 15 | 6.2 | 20:1 |
| 4 | 106 | 137 | 15 | 14.7 | 20:1 |
| 5 | 107 | 144 | 15 | 8.5 | 20:1 |
| 6 | 113 | 147 | 15 | 7.1 | 20:1 |
| 7 | 122 | 134 | 8.7 | 9.0 | 20:1 |
| 8 | 122 | 136 | 8.6 | 10.1 | 9:1 |
| 9 | 122 | 139 | 8.1 | 7.6 | 9:1 |
| 10 | 122 | 142 | 8.0 | 8.1 | 9:1 |
| 11 | 122 | 148 | 8.0 | 6.3 | 9:1 |
| 12 | 127 | 156 | 8.0 | 5.6 | 9:1 |
| 13 | 126 | 168 | 8.0 | 8.1 | 9:1 |
| 14 | 140 | 175 | 8.0 | 7.9 | 9:1 |
| 15 | 145 | 200 | 8.0 | 4.7 | 9:1 |

Fractions 3–6, when bulked, consist essentially of compounds having the structures:

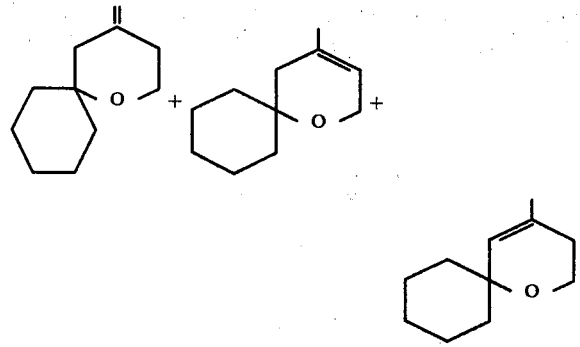

as confirmed by capillary GLC (conditions: SF-96 capillary column; 500'×0.03"; programmed 80°–185° C. at 2° C./minute), NMR, mass spectral and infra-red analyses.

The NMR spectrum for fractions 3–6 is set forth in FIG. 2.

Mass Spectral Data: Molecular ion, then, in decreasing order of intensity:

m/e = 166/123, 166, 68, 55, 41.

Infra-red Data:
755, 780, 810, 820, 840, 870, 875, 900, 960, 985, 1000, 1010, 1070, 1085, 1105, 1145, 1160, 1175, 1210, 1255, 1270, 1280, 1355, 1375, 1440, 1460, 2820, 2850, 2920, 3000.

| Nuclear Magnetic Resonance Data | Interpretation |
|---|---|
| 1.67 (s) | =C—CH₃— |
| 2.20–1.30 (m) | —CH₂— |
| 3.74 (diffuse t) | —CH₂—O— |
| 4.06 (m) | =C—CH₂—O |
| 4.70 (d) | —C=C with H |
| 5.26 (m) | Olefinic proton |

Fractions 8–12 consists essentially of the compound having the structure:

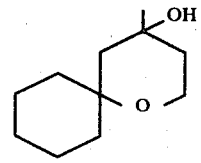

EXAMPLE II

PREPARATION OF 4-METHYL-1-OXASPIRO(5.5)UNDECANE

Reaction:

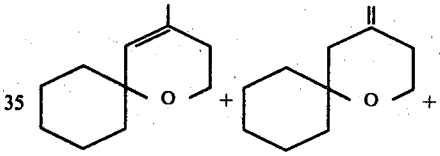

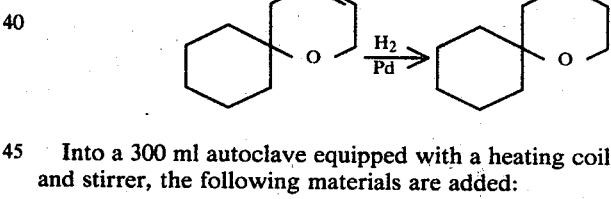

Into a 300 ml autoclave equipped with a heating coil and stirrer, the following materials are added:

| | |
|---|---|
| Isopropyl alcohol | 120 gms. |
| 5% Palladium on carbon catalyst | 0.8 gms. |
| Mixture of 4-methylene-1-oxaspiro[5.5]undecane, 4-methyl-1-oxaspiro[5.5]undec-3-ene and 4-methyl-1-oxaspiro[5.5]undec-4-ene produced according to Example I (Fractions 3–6) | 166 gms. |

The autoclave is then pressurized with hydrogen gas over a period of 11 hours and operated at 20°–30° C., periodically repressurizing the autoclave to 50 psig. After 11 hours, 1 mole of hydrogen is absorbed.

The contents of the autoclave is then filtered, the solvent stripped off and the material is then distilled through a 2" splash column after adding thereto 5 gms. of Primol ®, at a vapor temperature of 69°–71° C. and a pressure of 3.3–3.7 mm Hg.

This material consists essentially of a compound having the structure:

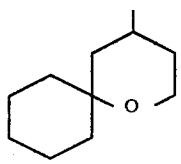

as confirmed by infra-red, mass spectral and NMR analyses.

The NMR Spectrum for Fraction 2 is set forth in FIG. 3.

Mass Spectral Data: Molecular ion, then, in order of decreasing intensity:

m/e=168/125, 55, 112, 41, 27, 39.

Infra-red Data:
500, 720, 820, 840, 880, 900, 970, 975, 980, 1045, 1060, 1080, 1100, 1120, 1140, 1175, 1185, 1260, 1290, 1300, 1375, 1440, 1450, 2850, 2920.

| NMR Data: | | |
|---|---|---|
| .86 (d) | $CH_3-\overset{H}{\underset{}{C}}$ | 3H |
| 2.04–1.00 (m) | Methylene and methine protons | 15H |
| 3.62 (m) | $-CH_2-O$ | 2H |

EXAMPLE III

DEHYDRATION OF 4-HYDROXY-4-METHYL-1-OXASPIRO(5.5)UNDECANE

Reaction:

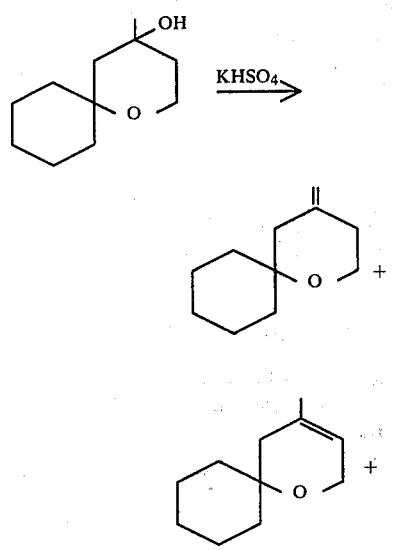

Into a 2 liter distillation flask fitted with a thermometer and a 12 inch Goodloe column (which in turn is fitted with an automatic head and fraction cutter) the following materials are placed:

| Amount | Ingredient |
|---|---|
| 1300 g | 4-hydroxy-4-methyl-1-oxaspiro (5.5) undecane |
| 65 g | Primol ® (See Note 3) |
| 65 g | KHSO₄ |
| 1 g | Ionol ® (See Note 4) |

Note 3: Primol ® is a registered trademark identifying a hydrocarbon mineral oil produced by Exxon Incorporation of Linden, New Jersey.
Note 4: Ionol ® is a registered trademark identifying the compound 2,6-di-t-butyl-4-methylphenol.

At 15 mm Hg pressure and a vapor temperature of 105°–113° C. the reaction mass is distilled yielding a mixture of compounds having the structures:

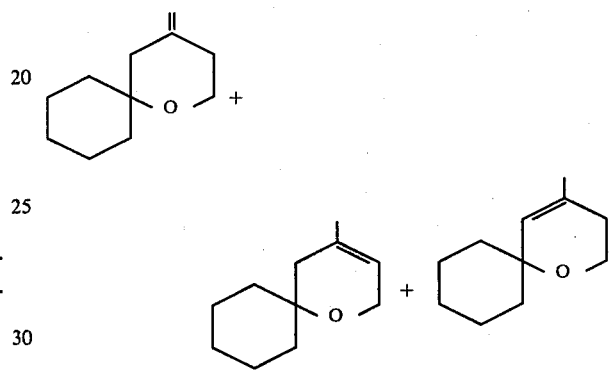

as confirmed by infrared analysis, mass spectral analysis and NMR analysis.

EXAMPLE IV

PREPARATION OF MIXTURE OF 2-METHYL-4-METHYLENE-1-OXASPIRO(5.-5)UNDECANE, 2,4-DIMETHYL-1-OXASPIRO(5.5)UNDEC-3-ENE, 2,4-DIMETHYL-1-OXASPIRO(5.5)UNDEC-4-ENE AND 2,4-DIMETHYL-4-HYDROXY-OXASPIRO(5.5)UNDECANE

Reaction:

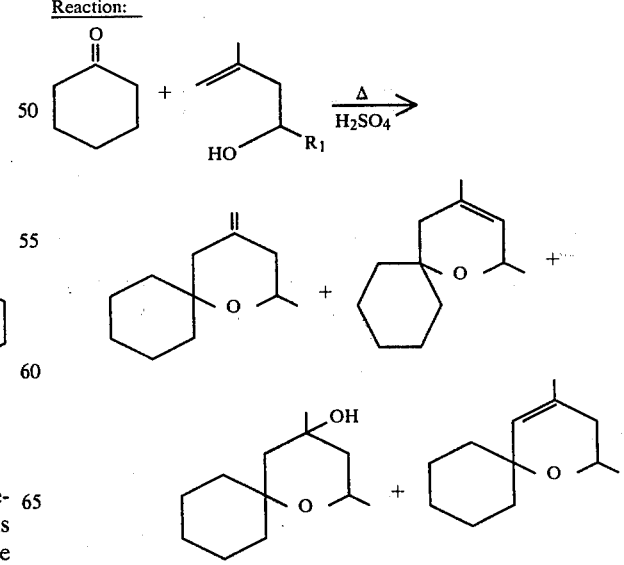

Into a 500 ml reaction flask equipped with stirrer, thermometer, Barrett trap reflux condenser and addition funnel is placed 490 gms. (5 moles) of cyclohexanone and 150 gm cyclohexane. The mixture is then heated to reflux and maintained at reflux. In a separate vessel, 597 gms. (5 moles) of 2-methyl-1-penten-4-ol, is placed, and 5 gm. concentrated sulfuric acid is added thereto dropwise while maintaining the temperature of 10° C. The resulting mixture of sulfuric acid and 2-methyl-1-penten-4-ol is then added over a period of one hour to the refluxing cyclohexanone. Refluxing is continued for a period of 4 hours. 85 ml H₂O is collected in the Barrett trap.

The reaction mass is then cooled to room temperature and 250 ml aqueous 10% NaOH is added thereto resulting in an aqueous and an organic phase. The organic phase is washed with one 250 ml portion of 10% aqueous sodium chloride.

The crude reaction product is stripped and rushed over after adding thereto 10 gms. of Primol ® and 0.1 gms. of Ionol ® at a vapor temperature of 55°–170° C.; a liquid temperature of 94°–200° C. and a vacuum of 15–7 mm Hg.

The rushed over material is then fractionated after adding thereto 10 gms. of Primol and 0.1 gms. of Ionox as follows:

| Fraction No. | Vapor Temp. | Liquid Temp. | Pressure (mm Hg) | Weight of Fraction | Reflux Ratio |
| --- | --- | --- | --- | --- | --- |
| 1 | 57–70° C. | 88–89° C. | 3.4–3.7 | 12.4 | 9:1 |
| 2 | 76 | 89 | 3.7 | 11.8 | 9:1 |
| 3 | 77 | 90 | 3.7 | 10.4 | 9:1 |
| 4 | 78 | 91 | 3.7 | 9.1 | 9:1 |
| 5 | 78 | 91 | 3.7 | 9.9 | 9:1 |
| 6 | 79 | 92 | 3.7 | 11.3 | 9:1 |
| 7 | 80 | 92 | 3.8 | 10.4 | 9:1 |
| 8 | 81 | 93 | 3.8 | 13.0 | 9:1 |
| 9 | 81 | 93 | 3.8 | 15.8 | 9:1 |
| 10 | 83 | 94 | 3.8 | 17.2 | 9:1 |
| 11 | 82 | 94 | 3.8 | 12.5 | 9:1 |
| 12 | 82 | 94 | 3.8 | 47.9 | 1:1 |
| 13 | 82 | 94 | 3.8 | 47.7 | 1:1 |
| 14 | 82 | 94 | 3.8 | 44.4 | 1:1 |
| 15 | 73 | 91 | 3.9 | 28.4 | 1:1 |
| 16 | 74 | 93 | 3.9 | 47.3 | 1:1 |
| 17 | 74 | 96 | 3.9 | 46.9 | 1:1 |
| 18 | 74 | 102 | 4.1 | 45.1 | 1:1 |
| 18 | 74 | 102 | 4.1 | 45.1 | 1:1 |
| 19 | 78 | 118 | 5.2 | 40.0 | 1:1 |
| 20 | 85 | 127 | 5.2 | 16.2 | 1:1 |
| 21 | 116 | 144 | 4.6 | 19.8 | 9:1 |
| 22 | 119 | 155 | 4.7 | 11.0 | 9:1 |
| 23 | 122 | 172 | 4.7 | 13.0 | 9:1 |
| 24 | 120 | 200 | 4.7 | 11.5 | 9:1 |

Fractions 15–19, as confirmed by infra-red, NMR and mass spectral analyses consists of more than 99% of a mixture of the compounds:

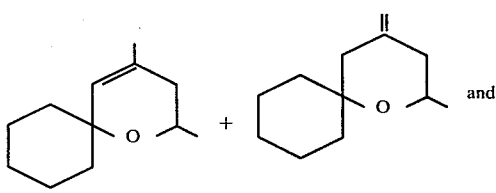

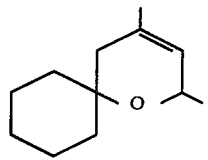

The NMR analysis data for Fraction 17 is set forth in FIG. 4.

Mass Spectral Data: Molecular ion, then in order of decreasing intensity:

m/e = 180/137, 67, 43, 82, 41, 81.

Infra-Red Data:
400, 820, 910, 1000, 1010, 1030, 1050, 1075, 1090, 1110, 1140, 1150, 1160, 1175, 1180, 1260, 1320, 1350, 1360, 1375, 1440, 2850, 2920, 2980.

| Nuclear Magnetic Resonance Data: | |
| --- | --- |
| 1.14 (d) | H<br>CH₃—C—O— |
| 1.16 (d) | H<br>CH₃—C—C—<br>\|<br>O |
| 1.62 (s) | =C—CH₃ |
| 1.98–1.40 (m) | —CH₂— |
| 3.60 (m) | \|<br>H—C—O— |
| 4.06 (m) | H<br>=C—C—O |
| 4.64 (d) | \|<br>—C=C—H<br>\|<br>H |
| 5.06 (m) | \| H<br>—C=C— |

Fractions 21–24 as confirmed by infrared, NMR and mass spectral analysis consists of the compound having the structure:

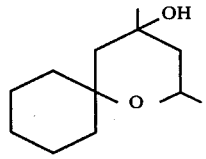

EXAMPLE V

PREPARATION OF 2,4-DIMETHYL-1-OXASPIRO(5.5)UNDECANE

Reaction:

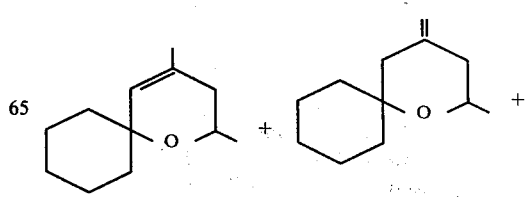

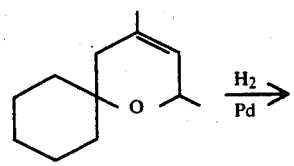

Into a 300 ml autoclave with a heating coil and shaker, the following materials are added:

| Ingredient | Amount |
|---|---|
| Isopropyl alcohol | 45 gms. |
| 5% Palladium on carbon catalyst | 0.6 gms. |
| Mixture of 2-methyl-4-methylene-1-oxaspiro[5.5]undecane, 2,4-dimethyl-1-oxaspiro[5.5]undec-3-ene and 2,4-dimethyl-1-oxaspiro[5.5]undec-4-ene produced according to Example IV | 45 gms. |

The autoclave is then pressurized with hydrogen gas and operated at 100° C. over a period of 21 hours periodically repressurizing the autoclave to 1000 psig.

The contents of the autoclave is then filtered and rushed over. The rushed over material is then distilled through a 2" splash column after adding thereto 5 gms. Primol ®, at a vapor temperature of 68° C. and a pressure of 3.0 mm Hg.

Infrared and NMR analyses confirm the structure of the resulting product as being:

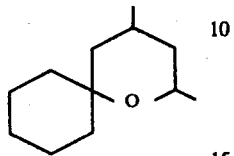

Infrared data:
810, 910, 990, 1000, 1030, 1040, 1055, 1070, 1090, 1105, 1120, 1130, 1165, 1185, 1235, 1240, 1350, 1370, 1440, 2860, 2920 cm$^{-1}$.

| Nuclear Magnetic Resonance Data: | | |
|---|---|---|
| ppm | | Interpretation |
| 0.87 | (d) | protons in position at "a" in above structure (—CH$_2$) |
| 1.14 | (d) | protons in position at "b" in above structure (—CH$_2$) |
| 2.00–1.30 | (m) | protons in positions at "c", "d", "e", "f", "g", "h", "i" (—CH$_2$) |
| 3.64 | (m) | H—C—O— |

EXAMPLE VI

DEHYDRATION OF 4-HYDROXY-2,4-DIMETHYL-1-OXASPIRO(5.5)UNDECANE

Reaction:

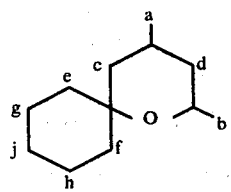

Into a 2 liter distillation flask fitted with a thermometer and a 12 inch Goodloe column (which in turn is fitted with an automatic head and fraction cutter) the following materials are placed:

| Amount | Ingredient |
|---|---|
| 1300 g | 4-hydroxy-2,4-dimethyl-1-oxaspiro(5.5) undecane |
| 65 g | Primol ® (See Note 5) |
| 65 g | KHSO$_4$ |
| 1 g | Ionol ® (See Note 6) |

Note 5: Primol ® is a registered trademark identifying a hydrocarbon mineral oil produced by Exxon Incorporation of Linden, New Jersey.
Note 6: Ionol ® is a registered trademark identifying the compound 2,6-di-t-butyl-4-methylphenol.

At 3.9–5.2 mm Hg pressure and a vapor temperature of 73° C.–78° C. the reaction mass is fractionated yielding a mixture of compounds having the structures:

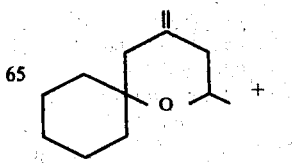

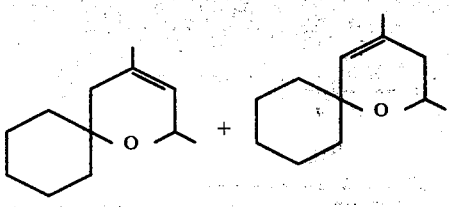

as confirmed by infrared analysis, mass spectral analysis and NMR analysis.

EXAMPLE VII

PREPARATION OF MIXTURE OF 8,8,10-TRIMETHYL-4-METHYLENE-1-OXASPIRO[5.5]UNDECANE; 4,8,8,10-TETRAMETHYL-1-OXASPIRO[5.5]UNDEC-3-ENE; 4,8,8,10-TETRAMETHYL-1-OXASPIRO[5.5]UNDEC-4-ENE AND 4-HYDROXY-4,8,8,10-TETRAMETHYL-1-OXASPIRO[5.5]UNDECANE

Reaction

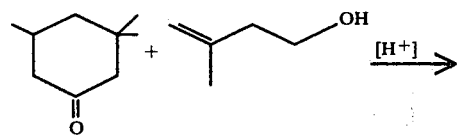

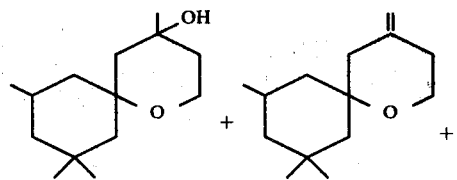

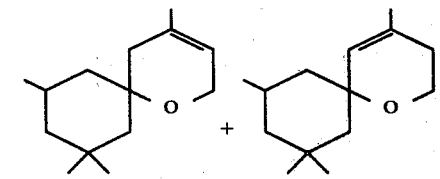

Into a 1 liter reaction flask equipped with stirrer, thermometer, reflux condenser and addition funnel is placed 250 gms. (1.95 moles) of 3,3,5-trimethyl cyclohexanone. In a separate vessel, 168 grams (1.95 moles) of 3-methyl-3-buten-1-ol is placed and 2 gms. of concentrated sulfuric acid is added thereto dropwise while maintaining the temperature of 10° C. The resulting mixture of sulfuric acid and 3-methyl-3-buten-1-ol is then added over a period of one hour to the 3,3,5-trimethyl cyclohexanone which has been preheated to 80°–85° C., while maintaining the temperature in the range of 80°–85° C.

After the addition the reaction mass is stirred at 80°–85° C. for a period of 9 hours.

The reaction mass is then cooled to room temperature and 100 ml of 10% aqueous NaOH is added thereto, yielding two phases; an aqueous and an organic phase. The organic phase is washed with one 100 ml portion of 10% aqueous sodium chloride.

The crude reaction product is then rushed over after adding thereto 10 gms. of Primol ® an 0.1 gms. of Ionol ® at a vapor temperature of 69°–153° C.; a liquid temperature of 75°–200° C. and a vacuum of 0.8–3.5 mm Hg.

The rushed over material is then fractionated after adding thereto 4.5 gms. of Primol ®, 0.1 gms. of Ionol ® and 0.5 gms. of triethanolamine as follows:

| Fraction No. | Vapor Temp. | Liquid Temp. | Pressure (mm Hg) | Weight of Fraction | Reflux Ratio |
|---|---|---|---|---|---|
| 1 | 49–51 | 74–76 | 3.7–3.4 | 19.3 | 20:1 |
| 2 | 51 | 77 | 3.7 | 20.1 | 20:1 |
| 3 | 51 | 79 | 4.0 | 20.3 | 20:1 |
| 4 | 51 | 83 | 3.9 | 19.5 | 20:1 |
| 5 | 51 | 88 | 4.0 | 22.3 | 20:1 |
| 6 | 51 | 98 | 4.0 | 22.4 | 20:1 |
| 7 | 54 | 107 | 4.0 | 6.1 | 20:1 |
| 8 | 68 | 110 | 3.0 | 6.7 | 20:1 |
| 9 | 74 | 116 | 3.0 | 3.5 | 20:1 |
| 10 | 82 | 120 | 3.0 | 8.4 | 20:1 |
| 11 | 82–89 | 111–113 | 3.5 | 20.1 | 20:1 |
| 12 | 90 | 118 | 3.6 | 26.7 | 20:1 |
| 13 | 92 | 129 | 3.7 | 21.3 | 20:1 |
| 14 | 106 | 141 | 3.7 | 9.8 | 20:1 |
| 15 | 115 | 154 | 3.5 | 6.8 | 20:1 |
| 16 | 118 | 163 | 3.5 | 12.8 | 20:1 |
| 17 | 146 | 189 | 3.5 | 13.3 | 20:1 |
| 18 | 162 | 202 | 3.0 | 6.0 | 20:1 |

Fraction 13 is confirmed by IR, mass spectral and NMR analyses to be a mixture of compounds having the structures:

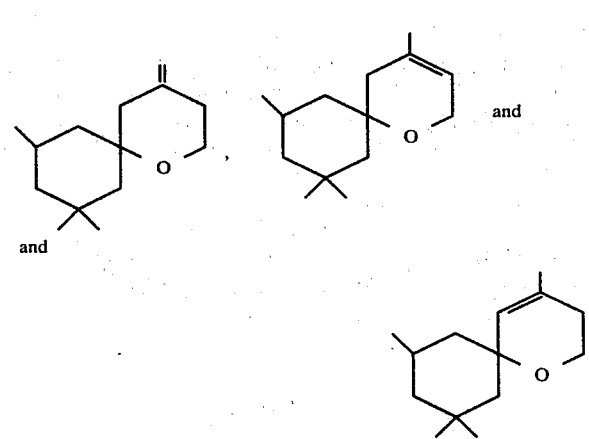

The NMR spectrum for Fraction 10 is set forth in FIG. 5.

Mass Spectral Data: Molecular ion, then in decreasing intensity:

m/e=208/137, 68, 41, 83, 69, 39.

Infra-Red Data:
820, 890, 960, 980, 1020, 1050, 1075, 1100, 1125, 1160, 1170, 1180, 1210, 1225, 1260, 1360, 1380, 1415, 1425, 1430, 2880, 2920, 2970.

| Nuclear Magnetic Resonance Data: | |
|---|---|
| 0.86 (doublets): (3H) | H<br>CH$_3$—C |
| 1.22 gem dimethyl protons (6H) | |
| 1.67 (3H) | =C—CH$_3$ |
| 2.44–1.68 methylene and methine protons | |
| 3.86 (m) | CH$_2$—O— |
| 4.14 (m) | =C—CH$_2$—O |

Nuclear Magnetic Resonance Data:

4.60 (d) 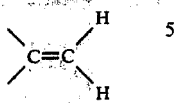

5.22 (m) olefinic proton

EXAMPLE VIII

DEHYDRATION OF 4-HYDROXY-4,8,8,10-TETRAMETHYL-1-OXAS-PIRO(5.5)UNDECANE

Reaction

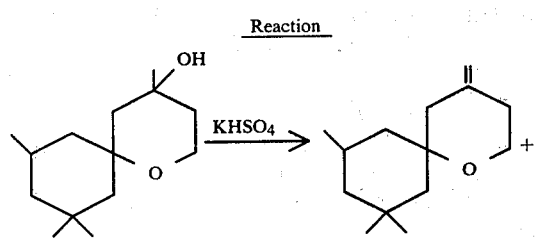

Into a 2 liter distillation flask fitted with a thermometer and a 12 inch Goodloe column (which in turn is fitted with an automatic head and fraction cutter) the following materials are placed:

| Amount | Ingredient |
|---|---|
| 1300 g | 4-hydroxy-4,8,8,10-tetramethyl-1-oxaspiro(5.5) undecane |
| 65 g | Primol ® (See Note 7) |
| 65 g | KHSO₄ |
| 1 g | Ionol ® (See Note 8) |

Note 7: Primol ® is a registered trademark identifying a hydrocarbon mineral oil produced by Exxon Inc. of Linden, New Jersey.

Note 8: Ionol ® is a registered trademark identifying the compound 2,6-di-t-butyl-4-methylphenol.

At 3.7 mm Hg pressure and a vapor temperature of 92° C. the reaction mass is fractionated yielding a mixture of compounds having the structures:

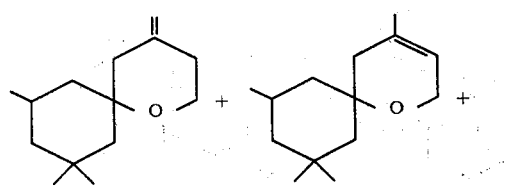

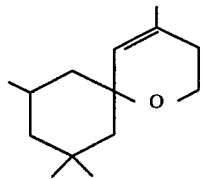

as confirmed by infrared analysis, mass spectral analysis and NMR analysis.

EXAMPLE IX

PREPARATION OF MIXTURE OF 9-t-BUTYL-4-METHYLENE-1-OXASPIRO[5.5]UN-DECANE; 9-t-BUTYL-4-METHYL-1-OXASPIRO[5.5]UNDEC-3-ENE; 9-t-BUTYL-4-METHYL-1-OXASPIRO[5.5]UNDEC-4-ENE; AND 9-t-BUTYL-4-HYDROXY-4-METHYL-1-OXAS-PIRO[5.5]UNDECANE

Reaction:

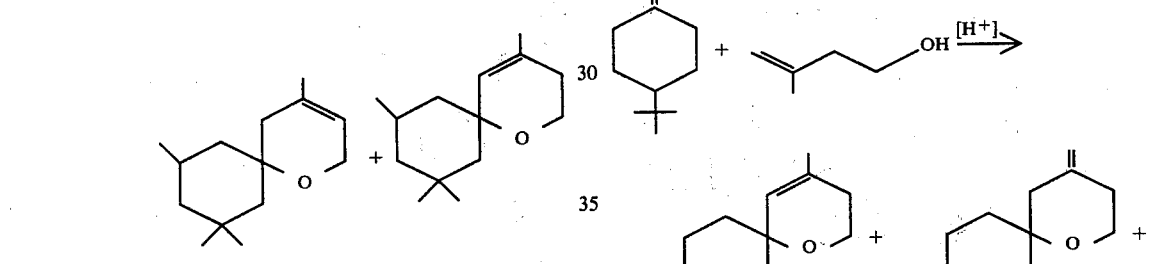

Into a 1 liter, 3-necked reaction flask equipped with stirrer, thermometer, reflux condenser and additional funnel is placed 284 gms. (2 moles) of t-butyl cyclohexanone. This mixture is then heated to 108° C. and maintained at that temperature. In a seaprate reaction vessel, is placed 172 gms (2 moles) of 3-methyl-3-buten-1-ol. 2 gms. of concentrated sulfuric acid is added thereto dropwise while maintaining the temperature of 10° C. The resulting mixture of sulfuric acid and 3-methyl-3-buten-1-ol is then added over a period of one hour to the t-butyl cyclohexanone solution, while maintaining the reaction mass temperature at reflux (about 108° C.).

After the addition, the reaction mass is stirred maintaining its temperature at about 108° C. for a period of about 4 hours.

The reaction mass is then cooled to room temperature and 2 g KOH is added thereto.

The crude reaction product is then rushed over after adding thereto 10 gms. of Primol ® and 0.1 gms. of Ionol ® at a vapor temperature of 105°–143° C.; a liquid temperature of 121°-200° C. and a vacuum of 2.9 mm Hg.

The rushed over material is then fractionated after adding thereto 4.5 gms. of Primol®, 0.1 gms. of Ionol® and 0.5 gms. of triethanolamine.

The fractional distillation data for the resulting reaction product is as follows:

| Fraction Number | Vapor Temp. | Liquid Temp. | Pressure (mm Hg) | Weight of Fr. | Reflux Ratio |
|---|---|---|---|---|---|
| 1 | 72°-105° C. | 126°-132° C. | 2.9 | 6.0 | 20:1 |
| 2 | 107 | 133 | 3.0 | 7.2 | 20:1 |
| 3 | 108 | 133 | 3.0 | 9.0 | 20:1 |
| 4 | 108 | 133 | 3.1 | 9.0 | 20:1 |
| 5 | 109 | 132 | 3.1 | 25.7 | 9:1 |
| 6 | 109 | 132 | 3.1 | 29.1 | 9:1 |
| 7 | 109 | 133 | 3.1 | 26.6 | 9:1 |
| 8 | 109 | 133 | 3.1 | 27.0 | 9:1 |
| 9 | 110 | 134 | 3.1 | 26.1 | 9:1 |
| 10 | 110 | 134 | 3.1 | 28.8 | 9:1 |
| 11 | 110 | 134 | 3.1 | 28.0 | 9:1 |
| 12 | 110 | 138 | 3.1 | 27.7 | 9:1 |
| 13 | 111 | 144 | 3.1 | 25.1 | 9:1 |
| 14 | 115 | 180 | 3.1 | 9.2 | 9:1 |
| 15 | 130 | 204 | 3.1 | 4.5 | 9:1 |

IR, NMR and mass spectral analysis confirms that the composition of bulked Fractions 5-14 consist of the following two compounds:

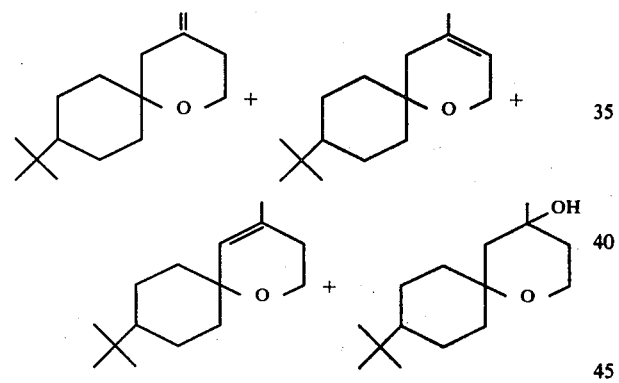

The NMR analysis for Fraction 13 is as follows:

| PEAK | INTERPRETATION |
|---|---|
| 0.80ppm(s) | CH$_3$<br>\|<br>CH$_3$—C—<br>\|<br>CH$_3$ |
| 1.66(broad) | =C—CH$_3$ |
| 2.00 - 1.00(m) | —CH$_2$— |
| 3.78(m) | CH$_2$—O— |
| 4.04(m) | =C—CH$_2$—O |
| 4.70(d) | —C=C(H)(H) |

The NMR spectrum for Fraction 13 is set forth in FIG. 6.

The infrared analysis for fraction 13 is as follows: 410, 780, 870, 930, 1010, 1035, 1080, 1105, 1145, 1160, 1195, 1215, 1240, 1360, 1380, 1390, 1440, 1465, 1475, 2820, 2860, 2930.

The infra red spectrum for Fraction 13 of this mixture is set forth in FIG. 7.

The mass spectral analysis for Fraction 13 is as follows: (molecular ion, then is decreasing intensity):

m/e=222/123, 41, 57, 68, 55, 67

Fraction 13 evaluated at 1 ppm has a weedy, green, herbaceous aroma and a taste which gives an initial sweet effect changing to an astringent note. At 5 ppm the mixture of Fraction 13 has a strong weedy, green aroma with vegetable green, over-ripe green pepper-like notes; and a taste wherein the vegetable character dominates having sweet artichoke-like undertones.

EXAMPLE X

DEHYDRATION OF 4-HYDROXY-4-METHYL-9-t-BUTYL-1-OXAS-PIRO(5.5)UNDECANE

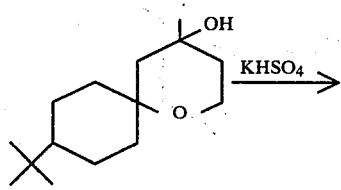

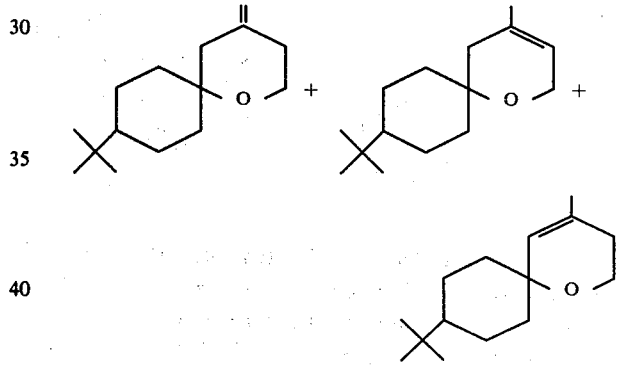

Into a 2 liter distillation flask fitted with a thermometer and a 12 inch Goodloe column (which in turn is fitted with an automatic head and fraction cutter) the following materials are placed:

| Amount | Ingredient |
|---|---|
| 1300g | 4-hydroxy-4-methyl-9-t-butyl-1-oxaspiro(5.5) undecane |
| 65 g | Primol® |
| 65 g | KHSO$_4$ |
| 1 g | Ionol® |

At 3.1 mm Hg pressure and a vapor temperature of 109°-115° C. the reaction mass is fractionated yielding a mixture of compounds having the structures:

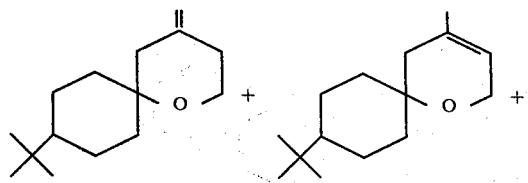

-continued

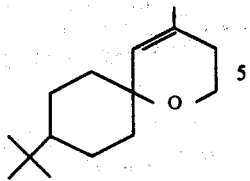

as confirmed by infrared analysis, mass spectral analysis and NMR analysis.

EXAMPLE XI

HYACINTH PERFUME FORMULATION

The following mixture is prepared:

| Ingredients | Parts by Weight |
|---|---|
| Cinnamic alcohol | 40 |
| Heliotropin | 20 |
| Galaxolide (50% in diethyl phthalate) (1,3,4,6,7,8-hexa-hydro-4,6,6,7,8,8-hexamethyl-cyclopenta-gamma-2-benzopyran) | 10 |
| Dimethyl hydroquinone | 5 |
| Indol | 2 |
| Lyral((4-(4-hydroxy-4-methyl-pentyl)-3-cyclohexane-10-carboxaldehyde) | 70 |
| Amyl cinnamic aldehyde | 20 |
| Hexyl cinnamic aldehyde | 70 |
| Phenylethyl alcohol | 150 |
| Benzyl alcohol | 25 |
| Benzyl acetate | 50 |
| Geraniol coeur | 10 |
| Citronellol coeur | 20 |
| Aubepine (para-methoxy benzaldehyde) | 15 |
| Benzyl salicylate | 5 |
| Eugenol | 10 |
| Methyl eugenol | 5 |
| Terpineol | 15 |
| Isoeugenol | 30 |
| Galbanum coeur | 10 |
| Methyl anthranilate | 2 |
| Ylang extra | 10 |
| Nerolidol | 40 |
| Phenyl ethyl salicylate | 40 |
| Mixture of 2-methyl-4-methylene-1-oxaspiro[5.5]undecane, 2,4-dimethyl-1-oxaspiro[5.5]undec-3-ene and 2,4-dimethyl-1-oxaspiro[5.5]undec-4-ene produced according to Example IV. | 15 |
| Mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene produced according to Example VII | 25 |

The mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane imparts a green, sweet, floral, herbaceous top note to the hyacinth perfume formulation. The mixture of 4,8,8,10-tetramethyl-1-oxaspiro[5.5]undec-3-ene, 4,8,8,10-tetramethyl-1-oxaspiro-[5.5]undec-4-ene and 8,8,10-trimethyl-4-methylene-1-oxaspiro[5.5]undecane imparts a green floral tone to the bottom note to the hyacinth perfume formulation.

EXAMPLE XII

GERANIUM PERFUME FORMULATION

The following mixture is prepared:

| Ingredients | Parts by Weight |
|---|---|
| Garaniol coeur | 200 |
| Citronellol coeur | 350 |
| Linalool | 15 |
| Citronellyl formate | 50 |
| Citronellyl acetate | 10 |
| Geranyl acetate | 50 |
| Benzyl butyrate | 5 |
| 4-Methyl-1-oxaspiro(5.5) undecane produced according to the process of Example II | 40 |

The 4-methyl-1-oxaspiro(5.5)undecane imparts the green, minty top note so necessary for geranium bourbon to the geranium perfume formulation.

EXAMPLE XIII

BASIL PERFUME FORMULATION

The following mixture is prepared:

| Ingredients | Parts by Weight |
|---|---|
| Linalool | 45 |
| Methyl chavicol | 20 |
| Eugenol | 3 |
| Isoeugenol | 1 |
| Terpineol | 5 |
| Bisaboline | 3 |
| Nerolidol | 1 |
| Mixture of 4-methylene-1-oxaspiro[5.5]undecane, 4-methyl-1-oxaspiro[5.5]undec-3-ene and 4-methyl-1-oxaspiro[5.5]undec-4-ene produced according to Example IV | 15 |

The mixture of 4-methylene-1-oxaspiro[5.5]undecane, 4-methyl-1-oxaspiro[5.5]undec-3-ene and 4-methyl-1-oxaspiro[5.5]undec-4-ene imparts the green, herbal top note of basil to the basil perfume formulation.

EXAMPLE XIV

USE OF 4-METHYL-1-OXASPIRO(5.5)UNDECANE AS FLAVORANT

4-Methyl-1-oxaspiro(5.5)undecane added at the rate of 0.3 ppm to a "low quality" cup of hot tea provided by a vending machine improves the aroma and taste of the tea substantially. The flavored and unflavored teas are compared by a 5-member bench panel. The flavored tea is unanimously considered by the bench panel as having a fresher, more aromatic, honey-like aroma and a more pleasant fresher, aromatic taste.

When the 4-methyl-1-oxaspiro(5.5)undecane is added to the tea at the rate of 10 ppm, a pleasant, minty, cooling note (which is preferred over menthol by 4 our of the 5 members of the bench panel) occurs. The 4-methyl-1-oxaspiro(5.5)undecane is considered to give rise to a novel type of "cooling" taste different from menthol.

EXAMPLE XV

RASPBERRY FLAVOR FORMULATION

The following formulation is prepared:

| Ingredient | Parts by Weight |
| --- | --- |
| Raspberry ketone (oxyphenylon) | 4 |
| Vanillin | 1 |
| Maltol | 2 |
| Alpha-ionone | 0.5 |
| Iso butylacetate | 20 |
| Ethylbutyrate | 5.5 |
| Dimethyl sulfide | 1 |
| Acetic acid | 30 |
| Acetaldehyde | 16 |
| Propylene glycol | 920 |

When added at the rate of 1% to the above formulation the 4-methyl-1-oxaspiro(5.5)undecane adds a more natural character thereto. A 5-member bench panel unanimously agrees that the formulation containing 1% of 4-methyl-1-oxaspiro(5.5)undecane is more raspberry-kernel like; more piney; has a wild raspberry or herbaceous taste and has a natural berry character. The flavor formulation containing the 1% of 4-methyl-1-oxaspiro(5.5)undecane is unanimously preferred over the flavor formulation not containing any 4-methyl-1-oxaspiro(5.5)undecane. The flavor formulations are compared side-by-side at the rate of 40 ppm in water.

EXAMPLE XVI

The following mixture is prepared:

| Ingredients | Parts by Weight |
| --- | --- |
| Natural Raspberry Concentrate Juice | 2½% |
| Water | 85% |
| Sugar syrup (37.5° Baume) | 12½% |

The wild raspberry, herbaceous and seedy, raspberry kernel notes of this raspberry juice is imparted in increased strength by addition of 4-methyl-1-oxaspiro(5.5)undecane at the rate of from 20 parts per million up to 50 parts per million.

EXAMPLE XVII

To the raspberry formulation of Example XV, 4-methyl-1-oxaspiro(5.5)undecane at the rate of 0.2% is added. This material is then called the "test composition". The raspberry formulation without 4-methyl-1-oxaspiro(5.5)undecane is called the "control composition".

The test and control compositions are added to the food products described hereinafter in the proportions shown for 10 kilograms of material to be flavored:

| Pudding | 5–10 grams (0.15–.1%) |
| --- | --- |
| Cooked sugar | 15–20 grams (.15–2%) |

Cooked sugar—100 ml of sugar syrup (prepared by dissolving 1 kilogram of sucrose in 600 ml of water) and 20 grams of glucose are mixed together and slowly heated to 145° C. The flavor is added and the mass allowed to cool and harden. Pudding—To 500 ml of warmed milk are added with stirring a mixture of 60 grams sucrose and 3 grams of pectin. The mixture is boiled for a few seconds and the flavor is added. The mixture was allowed to cool.

The finished foodstuff samples are tested by a panel of trained persons who express their views about the flavor of the samples. All members of the panel prefer the test samples having a more distinguished wild raspberry aroma with taste of the wild raspberries and its herbaceous and kernel notes.

EXAMPLE XVIII

A tobacco blend is made up by mixing the following materials:

| Ingredient | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes.

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the mixture of 4-methylene-1-oxaspiro(5.5)undecane, 4-methyl-1-oxaspiro(5.5)undec-3-ene and 4-methyl-1-oxaspiro[5.5]undec-4-ene produced according to Example I. at 100 ppm per cigarette. Another third of these model cigarettes are treated in the filter with the mixture of 4-methylene-1-oxaspiro[5.5]undecane, 4-methyl-1-oxaspiro[5.5]undec-3-ene and 4-methyl-1-oxaspiro[5.5]undec-4-ene at the rate of $2 \times 10^{-5}$ gm. and $3 \times 10^{-5}$ gm. When evaluated by paired comparison, the cigarettes treated both in the tobacco and in the filter with the mixture of 4-methyl-1-oxaspiro[5.5]undec-3-ene, 4-methyl-1-oxaspiro[5.5]undec-4-ene and 4-methylene-1-oxaspiro[5.5]undecane are found, in smoke flavor, to be more aromatic, more sweet, cooling (sensation in the mouth) and more tobacco like in character. In addition, there is a more cooling sensation in the aftertaste.

EXAMPLE XIX

A tobacco blend is made up by mixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

The above tobacco is used in producing cigarettes and the following formulation is compounded and incorporated into each of these cigarettes:

EXAMPLE XXX
COLOGNE

The composition of Example XIII is incorporated in a cologne at a concentration of 2.5% in 85% aqueous ethanol; and into a handkerchief perfume at a concentration of 20% (in 95% aqueous ethanol). A distinct and definite basil aroma with green, herbal top notes is imparted to the cologne and to the handkerchief perfume.

EXAMPLE XXXI
PREPARATION OF SOAP COMPOSITION

One hundred grams of soap chips are mixed with one gram of the mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I until a substantially homogeneous composition is obtained. The perfumed soap composition exhibits a green, basil, floral, herbal and eucalyptol-aroma.

EXAMPLE XXXII
PREPARATION OF A DETERGENT COMPOSITION

A total of 100 grams of a detergent powder is mixed with 0.15 grams of the mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I until a substantially homogeneous composition is prepared. This composition exhibits a green, basil, floral, herbal and eucalyptol-like aroma.

EXAMPLE XXXIII
PREPARATION OF A COSMETIC POWDER COMPOSITION

A cosmetic powder is prepared by mixing in a ball mill, 100 grams of talcum powder with 0.25 grams of the mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I. It has a pleasant green, basil-like, eucalyptol-like aroma with a floral undertone.

EXAMPLE XXXIV
PERFUMED LIQUID DETERGENT

Concentrated liquid detergent with a green, basil-like character is obtained containing 0.10%, 0.15% and 0.20% of the mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I. It is prepared by adding and homogeneously mixing the appropriate quantity of the mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I in the liquid detergent. The detergents all possess green, basil-like, floral notes, the intensity increasing with greater concentrations of the mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I.

EXAMPLE XXXV
COLOGNE

A mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I is incorporated in a cologne at a concentration of 2.5% in 85% aqueous ethanol; and into a handkerchief perfume at a concentration of 20% (in 95% aqueous ethanol). A distinct and definite basil-like, eucalyptol-like fragrance containing a green and floral top notes is imparted to the cologne and to the handkerchief perfume.

EXAMPLE XXXVI
PREPARATION OF SOAP COMPOSITION

One hundred grams of soap chips are mixed with one gram of 4-methyl-1-oxaspiro(5.5)undecane prepared according to Example II until a substantially homogeneous composition is obtained. The perfumed soap composition exhibits a basil-like, herbaceous and eucalyptol-like aroma.

EXAMPLE XXXVII
PREPARATION OF A DETERGENT COMPOSITION

A total of 100 grams of a detergent powder is mixed with 0.15 grams of 4-methyl-1-oxaspiro(5.5)undecane prepared according to Example II until a substantially homogeneous composition is prepared. This composition exhibits a basil-like, herbaceous and eucalyptol-like aroma.

EXAMPLE XXXVIII
PREPARATION OF A COSMETIC POWDER COMPOSITION

A cosmetic powder is prepared by mixing in a ball mill, 100 grams of talcum powder with 0.25 grams of 4-methyl-1-oxaspiro(5.5)undecane prepared according to Example II. It has a basil-like, herbaceous and eucalyptol-like aroma.

EXAMPLE XXXIX
PERFUMED LIQUID DETERGENT

Concentrated liquid detergent with a herbaceous character is obtained containing 0.10%, 0.15% and 0.20% of 4-methyl-1-oxaspiro(5.5)undecane prepared according to Example II. It is prepared by adding and homogeneously mixing the appropriate quantity of 4-methyl-1-oxaspiro(5.5)undecane prepared according to Example II in the liquid detergent. The detergents all possess basil-like, herbaceous and eucalyptol-like notes, the intensity increasing with greater concentrations of 4-methyl-1-oxaspiro(5.5)undecane prepared according to Example II.

EXAMPLE XL
COLOGNE

4-Methyl-1-oxaspiro(5.5)undecane prepared according to Example II is incorporated in a cologne at a concentration of 2.5% in 85% aqueous ethanol; and into a handkerchief perfume at a concentration of 20% (in 95% aqueous ethanol). A distinct and definite herbaceous fragrance containing basil-like and eucalyptol-like notes is imparted to the cologne and to the handkerchief perfume.

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the 4-methyl-1-oxaspiro(5.5)undecane produced according to Example II at 100 ppm per cigarette. Another third of these model cigarettes are treated in the filter with the 4-methyl-1-oxaspiro(5.5)undecane at the rate of $2 \times 10^{-5}$ gm. and $3 \times 10^{-5}$ gm. When evaluated by paired comparison the cigarettes treated both in the tobacco and in the filter with the 4-methyl-1-oxaspiro(5.5)undecane are found in smoke flavor to be more aromatic, more sweet, cooling (sensation in the mouth) and more tobacco like in character. In addition, there is a more cooling sensation in the aftertaste.

EXAMPLE XX

PREPARATION OF SOAP COMPOSITION

One hundred grams of soap chips are mixed with one gram of the perfume composition of Example XI until a substantially homogeneous composition is obtained. The perfumed soap composition exhibits a hyacinth fragrance containing an excellent green, floral and herbaceous notes so essential to orange flower.

EXAMPLE XXI

PREPARATION OF A DETERGENT COMPOSITION

A total of 100 grams of a detergent powder is mixed with 0.15 grams of the perfume composition of Example XI until a substantially homogeneous composition is prepared. This composition exhibits an hyacinth fragrance containing a green, floral and herbaceous notes essential to orange flower.

EXAMPLE XXII

PREPARATION OF A COSMETIC POWDER COMPOSITION

A cosmetic powder is prepared by mixing in a ball mill, 100 grams of talcum powder with 2 grams of the composition of Example XI. It has a hyacinth aroma with green, floral and herbaceous notes.

EXAMPLE XXIII

PERFUMED LIQUID DETERGENT

Concentrated liquid detergent with a hyacinth character is obtained containing 1.0%, 1.5% and 2.0% of the composition of Example XI. It is prepared by adding and homogeneously mixing the appropriate quantity of the composition of Example XI in the liquid detergent. The detergents all possess a hyacinth aroma with green, floral and herbaceous notes, the intensity increasing with greater concentrations of composition of Example XI.

EXAMPLE XXIV

COLOGNE

The composition of Example XI is incorporated in a cologne at a concentration of 2.5% in 85% aqueous ethanol; and into a handkerchief perfume at a concentration of 20% (in 95% aqueous ethanol). A distinct and definite hyacinth fragrance containing green, floral and herbaceous notes essential to hyacinth is imparted to the cologne and to the handkerchief perfume.

EXAMPLE XXV

COLOGNE

The composition of Example XII is incorporated in a cologne at a concentration of 2.5% in 85% aqueous ethanol; and into a handkerchief perfume at a concentration of 20% (in 95% aqueous ethanol). The composition of Example XII affords a distinct and definite geranium bourbon fragrance containing green, minty top notes found in geranium to the handkerchief perfume and cologne.

EXAMPLE XXVI

PREPARATION OF SOAP COMPOSITION

One hundred grams of soap chips are mixed with one gram of the perfume composition of Example XII until a substantially homogeneous composition is obtained. The perfumed soap composition exhibits a geranium bourbon fragrance having a green, minty top note.

EXAMPLE XXVII

PREPARATION OF A DETERGENT COMPOSITION

A total of 100 grams of a detergent powder is mixed with 0.15 grams of the perfume composition of Example XIII until a substantially homogeneous composition is prepared. This composition exhibits a basil fragrance having a green, herbal note.

EXAMPLE XXVIII

PREPARATION OF A COSMETIC POWDER COMPOSITION

A cosmetic powder is prepared by mixing in a ball mill, 100 grams of talcum powder with 2.5 grams of the perfume composition of Example XII. It has a geranium bourbon fragrance with a green, minty top note.

EXAMPLE XXIX

PERFUMED LIQUID DETERGENT

Concentrated liquid detergent with a basil fragrance having a green, herbal top note is obtained containing 1.0%, 1.5% and 2.0% of the composition of Example XIII. It is prepared by adding and homogeneously mixing the appropriate quantity of the composition of Example XIII in the liquid detergent. The detergents all possess a basil aromas and green, herbal top notes, the intensity increasing with greater concentrations of composition of Example XIII.

EXAMPLE XLI

PREPARATION OF SOAP COMPOSITION

One hundred grams of soap chips are mixed with one gram of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV until a substantially homogeneous composition is obtained. The perfumed soap composition exhibits a pleasant green, herbaceous, sweet oily, slightly minty aroma.

EXAMPLE XLII

PREPARATION OF A DETERGENT COMPOSITION

A total of 100 grams of a detergent powder is mixed with 0.15 grams of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV until a substantially homogeneous composition is prepared. This composition exhibits a green, herbaceous, sweet oily, slightly minty aroma.

EXAMPLE XLIII

PREPARATION OF A COSMETIC POWDER COMPOSITION

A cosmetic powder is prepared by mixing in a ball mill, 100 grams of talcum powder with 0.25 grams of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV. It has a pleasant green, herbaceous, sweet oily, slightly minty aroma.

EXAMPLE XLIV

PERFUMED LIQUID DETERGENT

Concentrated liquid detergent with a herbaceous character is obtained containing 0.10%, 0.15% and 0.20% of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV. It is prepared by adding and homogeneously mixing the appropriate quantity of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV in the liquid detergent. The detergents all possess a green, herbaceous, sweet oily, slightly minty aroma, the intensity increasing with greater concentrations of the mixture of 2,4-dimethyl-1-oxaspiro[5.5]undec-3-ene, 2,4-dimethyl-1-oxaspiro[5.-5]undec-4-ene and 2-methyl-4-methylene-1-oxaspiro[5.-5]undecane prepared according to Example IV.

EXAMPLE XLV

COLOGNE

The mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV is incorporated in a cologne at a concentration of 2.5% in 85% aqueous ethanol; and into a handkerchief perfume at a concentration of 20% (in 95% aqueous ethanol). A distinct and definite herbaceous fragrance containing a sweet, minty and green top notes is imparted to the cologne and to the handkerchief perfume.

EXAMPLE XLVI

PREPARATION OF SOAP COMPOSITION

One hundred grams of soap chips are mixed with one gram of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII until a substantially homogeneous composition is obtained. The perfumed soap composition exhibits a pleasant green, floral, minty and terpineol-like aroma.

EXAMPLE XLVII

PREPARATION OF A DETERGENT COMPOSITION

A total of 100 grams of a detergent powder is mixed with 0.15 grams of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII until a substantially homogeneous composition is prepared. This composition exhibits a pleasant green, floral, minty and terpineol-like aroma.

EXAMPLE XLVIII

PREPARATION OF A COSMETIC POWDER COMPOSITION

A cosmetic powder is prepared by mixing in a ball mill, 100 grams of talcum powder with 0.25 grams of the mixture of 8,8,10-trimethyl-4-methylene-1-oxaspiro[5.5]undecane, 4,8,8,10-tetramethyl-1-oxaspiro[5.-5]undec-3-ene and 4,8,8,10-tetramethyl-1-oxaspiro[5.-5]undec-4-ene prepared according to Example VII. It has a green, floral, minty and terpineol-like aroma.

EXAMPLE XLIX

PERFUMED LIQUID DETERGENT

Concentrated liquid detergent with a green, minty character is obtained containing 0.10%, 0.15% and 0.20% of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII. it is prepared by adding and homogeneously mixing the appropriate quantity of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII in the liquid detergent. The detergents all possess a green, floral, minty and terpineol-like aroma, the intensity increasing with greater concentrations of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII.

EXAMPLE L

COLOGNE

The mixture of 8,8,10-trimethyl-4-methylene-1-oxaspiro[5.5]undecane, 4,8,8,10-tetramethyl-1-oxaspiro[5.-5]undec-3-ene and 4,8,8,10-tetramethyl-1-oxaspiro[5.-5]undec-4-ene prepared according to Example VII is incorporated in a cologne at a concentration of 2.5% in 85% aqueous ethanol; and into a handkerchief perfume at a concentration of 20% (in 95% aqueous ethanol). A distinct and definite green, minty flower fragrance containing a terpineol-like top note is imparted to the cologne and to the handkerchief perfume.

EXAMPLE LI

The following materials are compared from a food flavor standpoint:

(iii) Mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene; and (iv) Mixture of 9-t-butyl-4-methylene-1-oxaspiro[5.5]undecane, 4-methyl-9-t-butyl-1-oxaspiro[5.5]undec-3-ene and 4-methyl-9-t-butyl-1-oxaspiro[5.5]undec-4-ene.

and such differences are unobvious and unexpected.

| Spiropyran Material | Structure Representation | Flavor Properties | Fragrance Properties |
|---|---|---|---|
| (i) Mixture of 4-methylene-1-oxaspiro[5.5]4-methyl-1-oxaspiro(5.5)undec-3-ene and 4-methyl-1-oxaspiro[5.5]undec-4-ene | | A dill, basil, valerian oil aroma with caraway nuances and dill, basil, valerian oil taste with a thyme-like and piney character. | Heady, green basil, floral, herbal and eucalyptol notes. |
| (ii) Mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane | | Ionone, tea, and red-berry aroma with herbaceous, "damascenone-like,"floral, sweet, fruity, woody and apple-like nuances and woody, petitgrain-like, fruity taste with apple-like, smokey and astringent notes. | Green, herbaceous, sweet, oily, slightly minty aroma with "pickled," green olive top notes. |
| (iii) Mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene | | Green, leafy, minty, parsley-like aroma with green, minty, herbaceous parsley-like flavor. | Green, floral, minty and terpineol-like notes. |
| (iv) Mixture of 9-t-butyl-4-methylene-1-oxaspiro[5.5]undecane, 4-methyl-9-t-butyl-oxaspiro[5.5]undec-3-ene and 4-methyl-9-t-butyl-1-oxaspiro[5.5]undec-4-ene | | Salicylate floral aroma with a green/woody undertone and a salicylate-like, oily floral herbaceous taste. | Green, floral and warm linen notes. |
| (v) 4-methyl-1-oxaspiro[5.5]undecane | | Sweet, floral, fruity, minty, vanillin-like aroma with blackberry, berry and herbaceous notes; and a minty cooling taste with eucalyptol, pinry, basil and herbaceous notes. | Basil, herbaceous, and eucalyptol notes. |

Only solution (v) has a strong mint/cooling aroma and taste which are missing from solutions (i), (ii), (iii) and (iv) and these organoleptic characteristics are unexpected, unobvious and advantageous and cause compound (v) to have potenti uses in the mint flavor area, berry flavors "cough" candy flavors.

Thus, 4-methyl-1-oxaspiro[5.5]undecane is unexpectedly and advantageously useful for minty flavors given the flavor properties of compounds having the structures similar to this compound; namely:

(i) Mixture of 4-methylene-1-oxaspiro[5.5]undecane, 4-methyl-1-oxaspiro[5.5]undec-3-ene and 4-methyl-1-oxaspiro[5.5]undec-4-ene;

(ii) Mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane;

BRIEF DESCRIPTION OF THE DRAWINGS

FIG. 4 represents the NMR spectrum for fraction 17 of Example IV.

FIG. 5 sets forth the NMR spectrum for fraction 10 produced according to Example VII.

Figure 1:
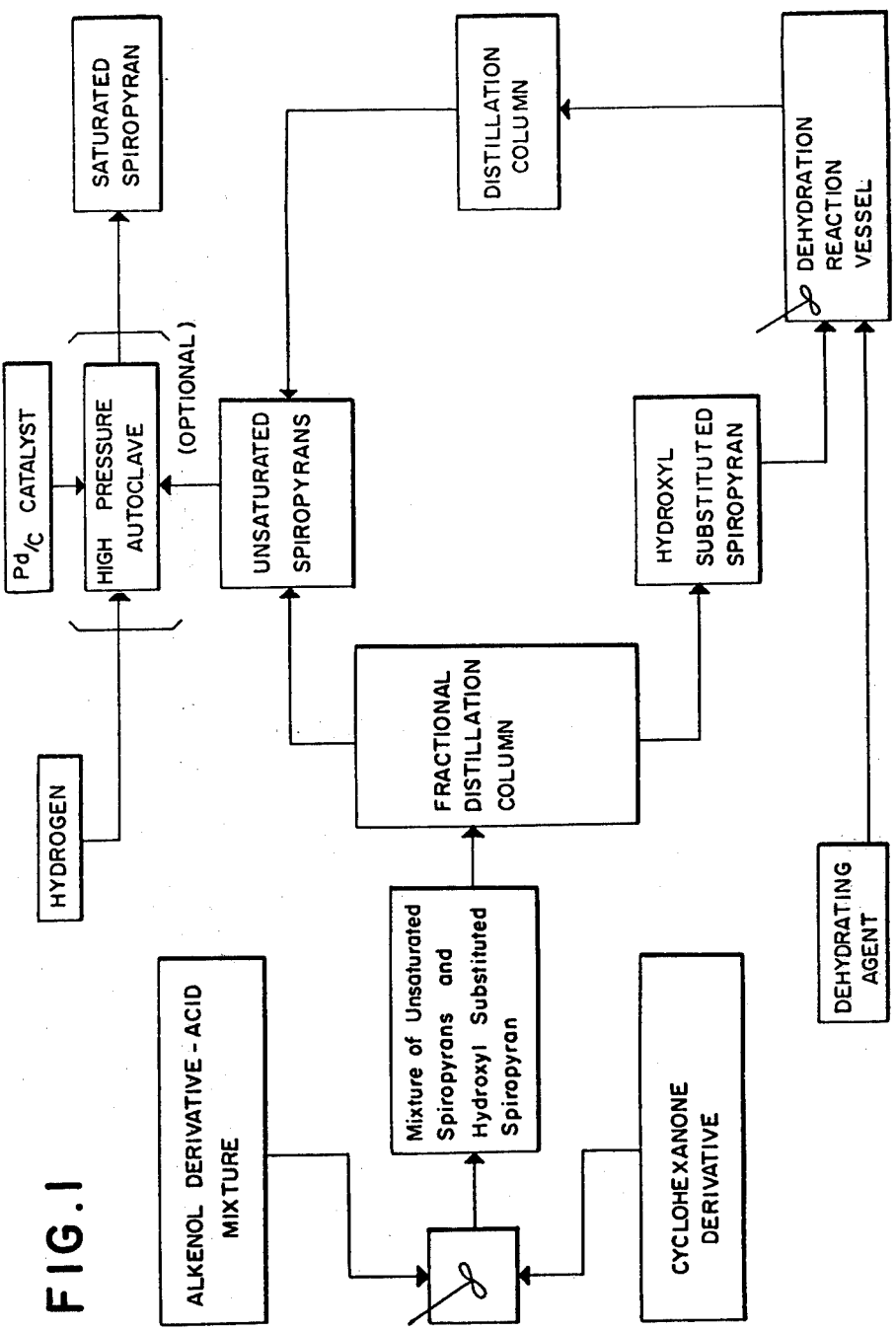
FIG. 1 is a schematic block diagram setting forth the steps of the process of our invention.
Figure 2:
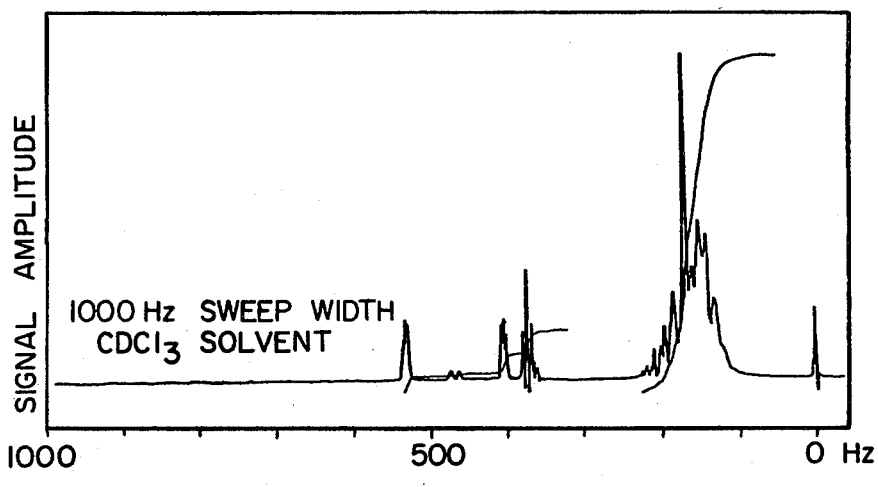
FIG. 2 sets forth the NMR spectrum for fractions 3–6 produced according to Example I.
Figure 3:
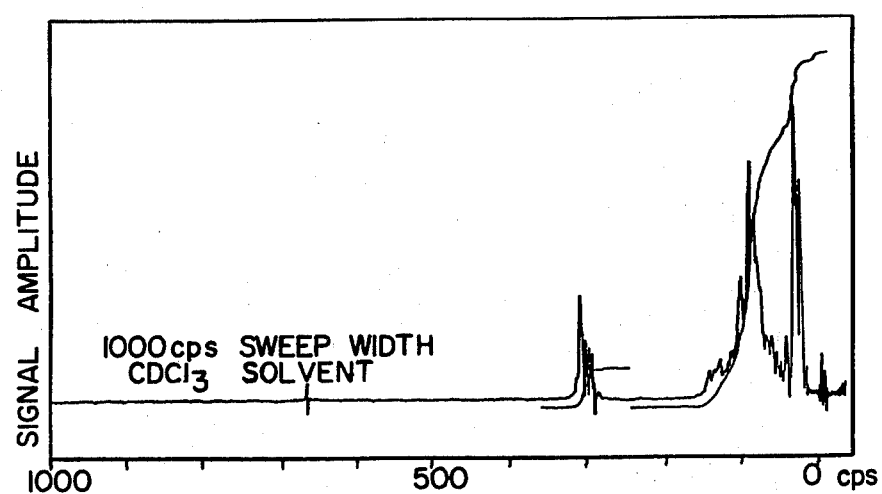
FIG. 3 sets forth the NMR spectrum for fraction 2 produced according to Example II.
Figures 6, 7:
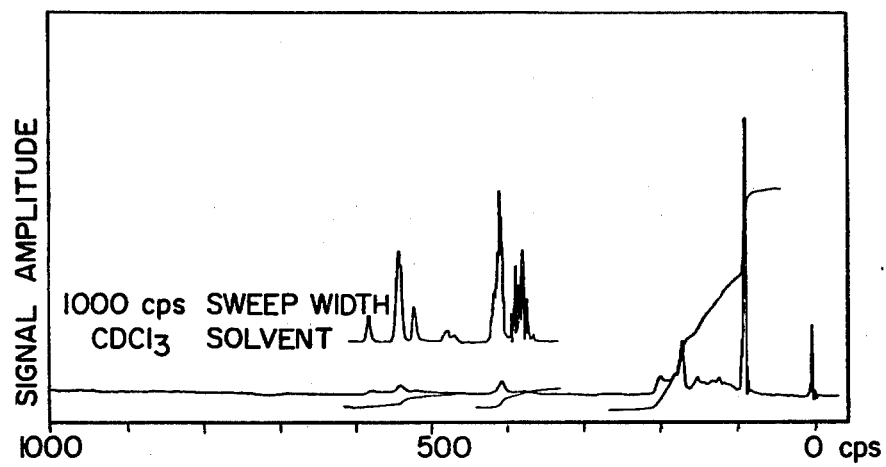
FIG. 6 sets forth the NMR spectrum for fraction 13 produced according to Example IX.
FIG. 7 sets forth the infrared spectrum for fraction 1 produced according to Example IX.

What is claimed is:

1. A process for preparing a solid or liquid detergent comprising the step of intimately admixing with a solid or liquid detergent base from 100 parts per million up to 3.0% by weight of said detergent of a spiropyran composition comprising at least one substance selected from the group consisting of:

(i) a spiropyran compound having the structure:

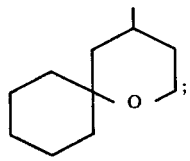

(ii) a mixture of spiropyrans having the structures:

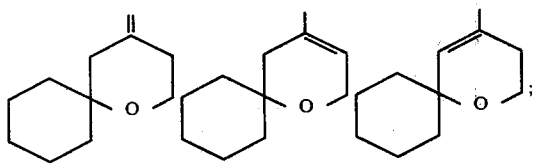

(iii) a mixture of spiropyrans having the structures:

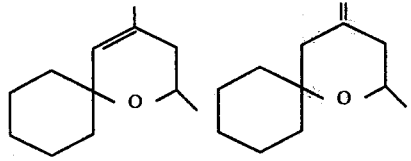

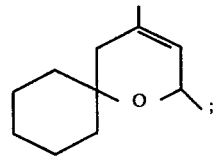

and (iv) a mixture of spiropyran compounds having the structures:

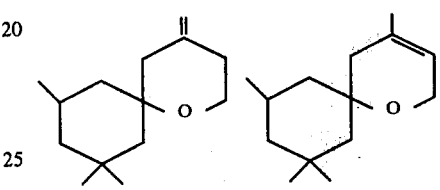

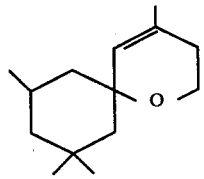

* * * * *